(12) United States Patent
Xia et al.

(10) Patent No.: US 8,440,326 B2
(45) Date of Patent: May 14, 2013

(54) HOLE TRANSPORT MATERIALS CONTAINING TRIPHENYLENE

(75) Inventors: Chuanjun Xia, Lawrenceville, NJ (US); Raymond Kwong, Plainsboro, NJ (US)

(73) Assignee: Universal Display Corporation, Ewing, NJ (US)

( * ) Notice: Subject to any disclaimer, the term of this patent is extended or adjusted under 35 U.S.C. 154(b) by 88 days.

(21) Appl. No.: 13/001,949

(22) PCT Filed: Jun. 30, 2009

(86) PCT No.: PCT/US2009/049188
§ 371 (c)(1),
(2), (4) Date: Apr. 4, 2011

(87) PCT Pub. No.: WO2010/002850
PCT Pub. Date: Jan. 7, 2010

(65) Prior Publication Data
US 2011/0180786 A1    Jul. 28, 2011

Related U.S. Application Data

(60) Provisional application No. 61/077,095, filed on Jun. 30, 2008.

(51) Int. Cl.
*H01L 51/54* (2006.01)
(52) U.S. Cl.
USPC ........... 428/690; 428/917; 313/504; 313/505; 313/506; 564/426; 564/434
(58) Field of Classification Search .................. 428/690, 428/917; 313/504, 505, 506; 564/426, 434, 564/26
See application file for complete search history.

(56) References Cited

U.S. PATENT DOCUMENTS

| 4,769,292 A | 9/1988 | Tang et al. |
| 5,061,569 A | 10/1991 | VanSlyke et al. |
| 5,247,190 A | 9/1993 | Friend et al. |

(Continued)

FOREIGN PATENT DOCUMENTS

| EP | 0650955 | 5/1995 |
| EP | 1725079 | 11/2006 |

(Continued)

OTHER PUBLICATIONS

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

(Continued)

*Primary Examiner* — Jennifer Chriss
*Assistant Examiner* — Gregory Clark
(74) *Attorney, Agent, or Firm* — Duane Morris LLP

(57) ABSTRACT

Novel materials are provided, having a single phenyl or chain of phenyls where there is a nitrogen atom on each end of the single phenyl or chain of phenyls. The nitrogen atom may be further substituted with particular triphenylene groups. Organic light-emitting devices are also provided, where the novel materials are used as a hole transport material in the device. Combinations of the hole transport material with specific host materials are also provided.

20 Claims, 3 Drawing Sheets

U.S. PATENT DOCUMENTS

| | | |
|---|---|---|
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0088728 A1 | 4/2006 | Kwong et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1* | 12/2006 | Kwong et al. ............... 428/690 |
| 2007/0088167 A1 | 4/2007 | Lin et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0261076 A1 | 10/2008 | Kwong et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| JP | 2000-299497 | 10/2000 |
| JP | 200511610 | 1/2005 |
| JP | 2005071983 | * 3/2005 |
| JP | 2007123392 | 5/2007 |
| JP | 2007254297 | 10/2007 |
| JP | 2008074939 | 10/2009 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008/073440 | 6/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009050290 | 4/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru$^{II}$ PHosphorescent Emitters," *Adv. Mater.*, 17(8)1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

MA, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2)156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1)162-164 (2002).

Holmes, R.J. et al., "Blue Organic Electrophosphorescence Using Exothermic Host-Guest Energy Transfer," *Appl. Phys. Lett.*, 82(15)2422-2424 (2003).

Sotoyama, Wataru et al., "Efficient Organic Light-Emitting Diodes with Phosphorescent Platinum Complexes Containing $N^\wedge$ $C^\wedge$ N-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11)1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16)3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5"Bis(dimesitylboryl)-2,2':5',2"-terthiophene as a Novel Family of Electron-Transporting Amorphous Molecular Materials," *J. Am. Chem. Soc.*, 120 (37):9714-9715 (1998).

Sakamoto,Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 3, 4-6 (1999).

U.S. Appl. No. 61/013,391, filed Dec. 28, 2007.

U.S. Appl. No. 61/077,095, filed Jun. 30, 2008.

Search Report in Chinese Application No. 200980132487.

* cited by examiner (Formula I)

S-2

S-3

S-4

HOLE TRANSPORT MATERIALS CONTAINING TRIPHENYLENE

This application is a National Stage of International Application No. PCT/US2009/049188, filed Jun. 30, 2009, which claims priority to U.S. Patent Application No. 61/077,095, filed on Jun. 30, 2008, the disclosures of which are incorporated herein by reference in their entirety.

This application claims priority to and benefit under 35 U.S.C. §119(e) to U.S. Provisional Application Ser. No. 61/077,095, filed Jun. 30, 2008, the disclosure of which is herein expressly incorporated by reference in its entirety.

This claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel materials. More specifically, the present invention relates to novel materials useful in organic light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)₃, which has the structure:

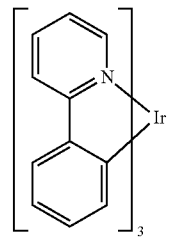

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand is referred to as "photoactive" when it is believed that the ligand contributes to the photoactive properties of an emissive material.

More details on OLEDs, and the definitions described above, can be found in U.S. Pat. No. 7,279,704, which is incorporated herein by reference in its entirety.

SUMMARY OF THE INVENTION

Novel materials are provided, having the chemical structure:

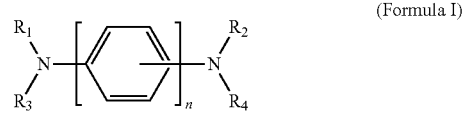

(Formula I)

n is 1, 2 or 3, and the phenyl rings between the nitrogen atoms may be attached to each other and to the nitrogen atoms in a para or meta configuration independently selected for each attachment. Each of $R_1$, $R_2$, $R_3$ and $R_4$ are independently selected from the group consisting of:

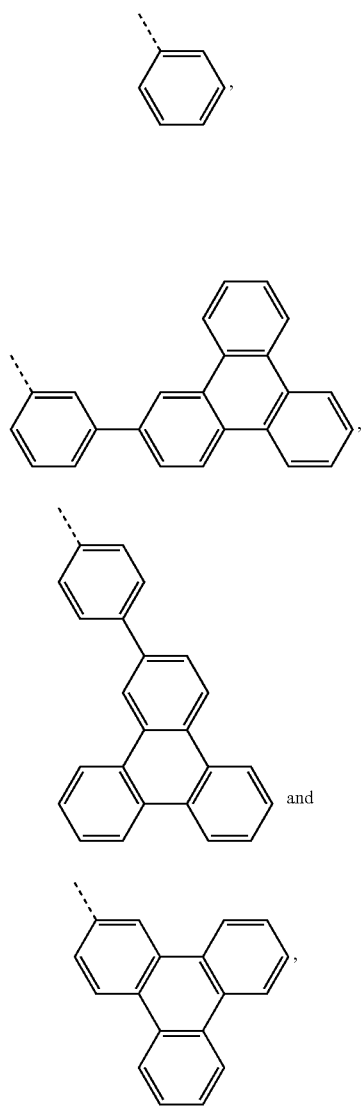

where the dotted line shows the point of attachment to a nitrogen atom of Formula I. At least one of $R_1$, $R_2$, $R_3$ and $R_4$ is selected from the group consisting of:

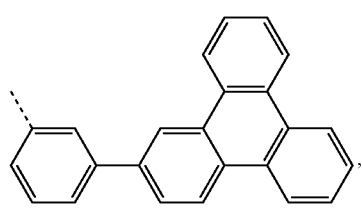

$R_1$, $R_2$, $R_3$ and $R_4$ are not all the same. Preferably, at least one of $R_1$, $R_2$, $R_3$ and $R_4$ is S-2. Preferably, at least one of $R_1$, $R_2$, $R_3$ and $R_4$ is S-3. Preferably, at least one of $R_1$, $R_2$, $R_3$ and $R_4$ is S-4. Each of $R_1$, $R_2$, $R_3$ and $R_4$ may be further substituted with substituents that are not fused to $R_1$, $R_2$, $R_3$ and $R_4$.

In one aspect, the compositions of matter provided having the structure of Formula I more specifically have the chemical structure of Formula II.

In another aspect, each of $R_1$, $R_2$, $R_3$ and $R_4$ is selected from the group consisting of S-1 though S-6.

Specific compositions of matter having Formula I are also provided, including compositions of matter having a structure selected from the group consisting of A-1 through A-6. Preferably, the composition of matter has the structure A-1 or A-5. Additionally, specific compositions of matter having Formula I are also provided, including compositions of matter having a structure selected from the group consisting of B-1 through B-6. Moreover, specific compositions of matter having Formula I are also provided, including compositions of matter having a structure selected from the group consisting of C-1 through C-6. Preferably, the composition of matter has the structure C-6.

Organic light-emitting devices and consumer products containing such devices are also provided, where the novel materials are used as a hole transport material in the device. Selections for the composition of matter having the structure of Formula I described as preferred for use in the materials having Formula I are also preferred for use in a device or consumer product that includes a composition of matter having the structure of Formula I. These selections include those for the substituents $R_1$, $R_2$, $R_3$, and $R_4$, Formula II, and structures A-1 though A-6, B-1 through B-6, and C-1 through C-6.

Combinations of the hole transport material with specific host materials are also provided. In one aspect, the host is a compound comprising a triphenylene containing benzo-fused thiophene. Preferably, the host is Compound 3. In another aspect, the host is an aryltriphenylene compound. Preferably, the host is Compound 2.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
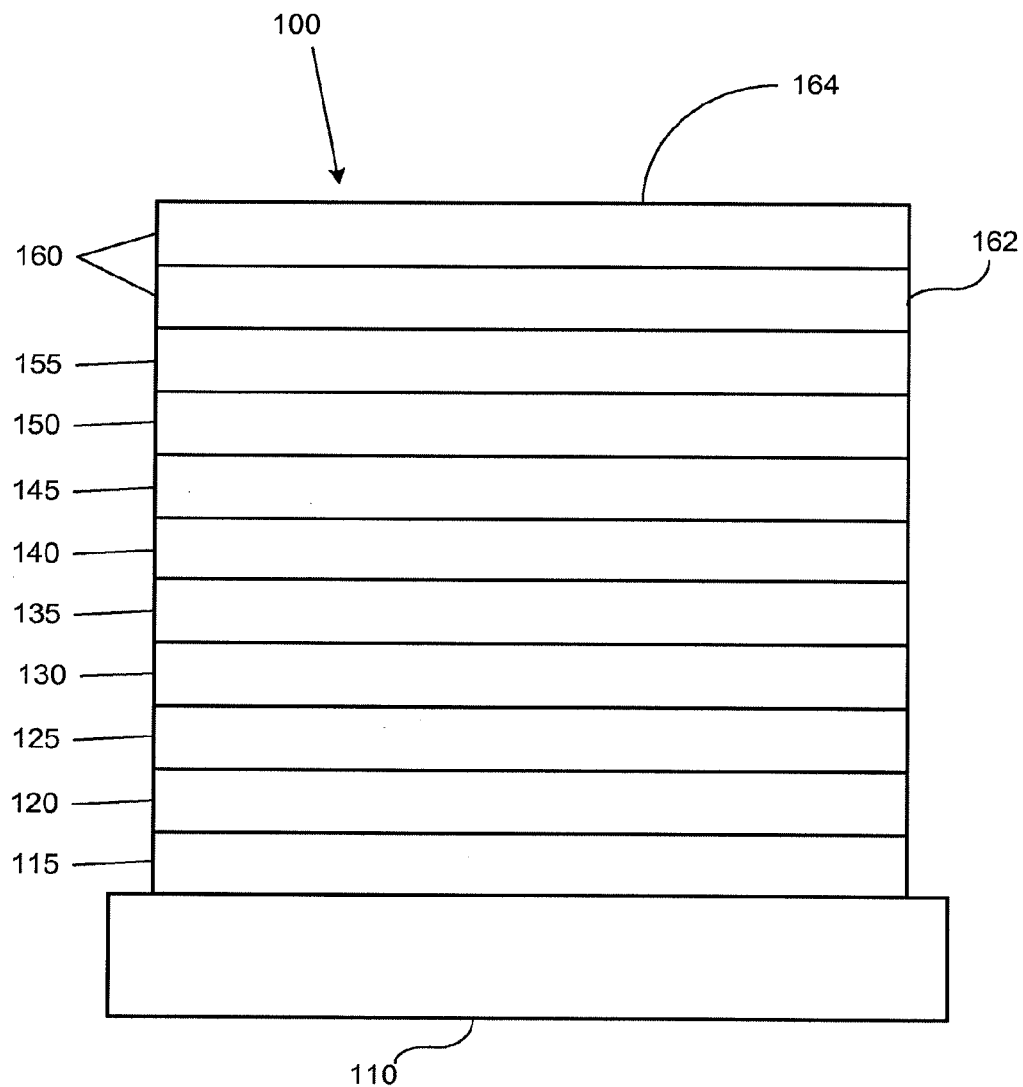
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
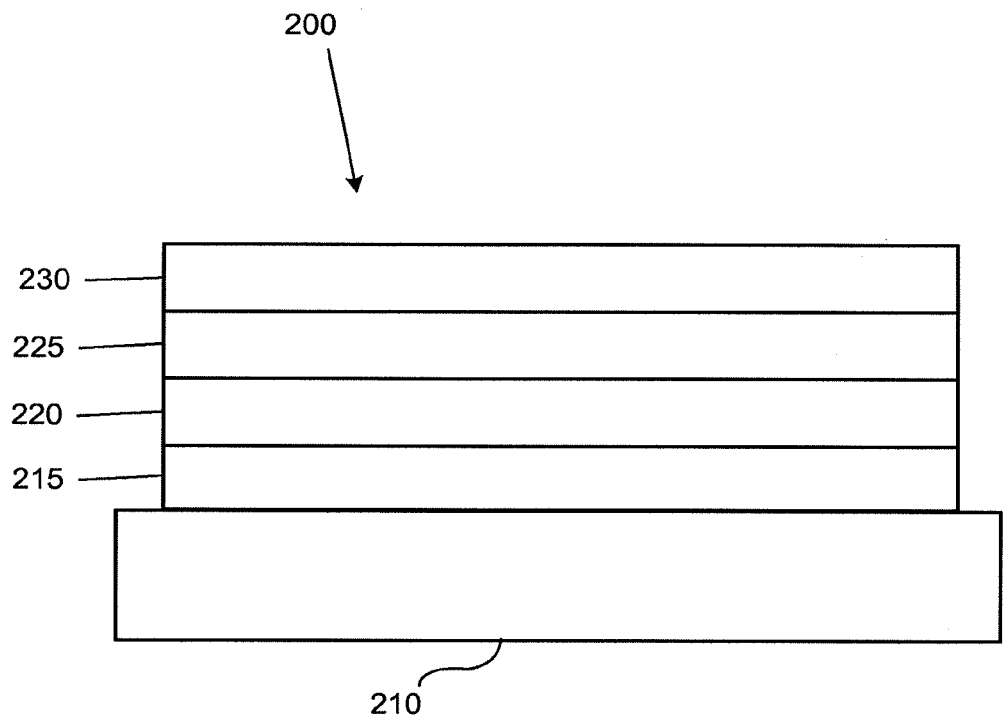
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A novel composition of matter is provided. The novel composition of matter includes a "core" similar to that of naphthylphenylbiphenyl diamine (NPD). As used herein, the core of NPD has two nitrogen atoms connected to each other by two phenyl rings, all connected in the para position. Novel compositions of matter are provided having more possibilities for the core, including two nitrogen atoms connected by 1, 2 or 3 phenyl rings, where each connection may independently be para or meta. At least one group attached to a nitrogen atom of the core includes a triphenylene group. Thus, a novel composition of matter is provided having the structure:

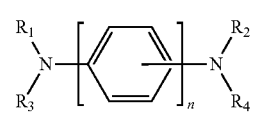
(Formula I)

where n is 1, 2 or 3, and the phenyl rings between the nitrogen atoms may be attached to each other and to the nitrogen atoms in a para or meta configuration independently selected for each attachment. Each of $R_1$, $R_2$, $R_3$ and $R_4$ is independently selected from the group consisting of:

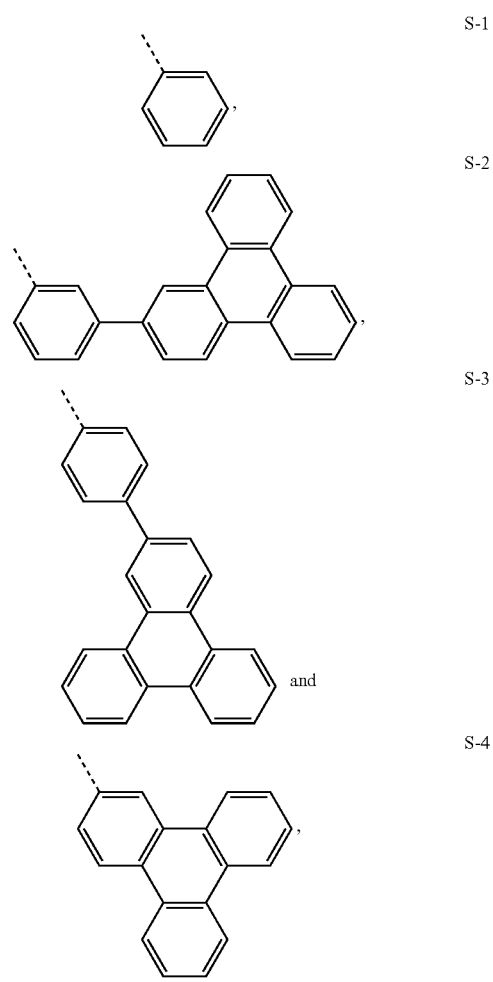

where the dotted line shows the point of attachment to a nitrogen atom of Formula I. At least one of $R_1$, $R_2$, $R_3$ and $R_4$ is selected from the group consisting of:

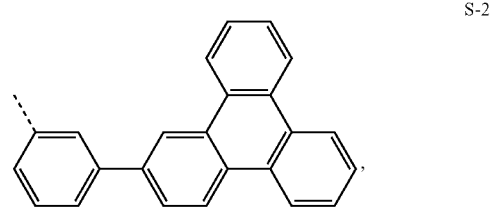

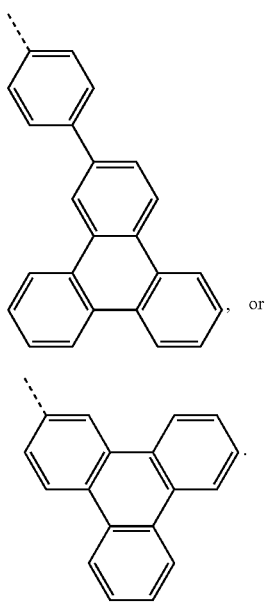

Figure 3:
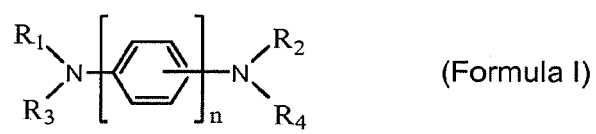
FIG. 3 shows chemical structures.
Figure 3:
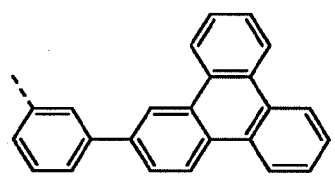
Figure 3:
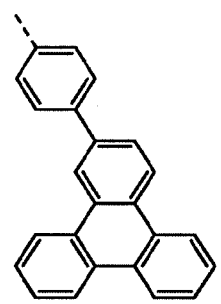
Figure 3:
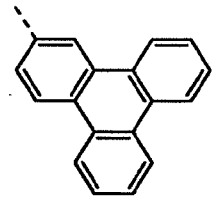

$R_1$, $R_2$, $R_3$ and $R_4$ are not all the same. Each of $R_1$, $R_2$, $R_3$ and $R_4$ may be further substituted with substituents that are not fused to $R_1$, $R_2$, $R_3$ and $R_4$. FIG. 3 shows chemical structures relevant to some compositions of matter described herein.

Without being limited to any theory as to why the novel materials are desirable, it is believed that the benzidine (4,4'-diaminobiphenyl) core, along with the variations described herein, are particularly desirable. Benzidine with one phenyl and one 1-naphthyl attached to each of the nitrogens is α-NPD, which is a widely used hole transport layer in OLEDs, and it is believed that the core contributes to the desirability of NPD. However, NPD does not work well in certain devices, particularly blue and green devices, which have higher energy triplets and charge carriers. It is believed that the napthyl group of NPD, in connection with high energy charge carriers and triplets, may be responsible for this instability, and that a triphenylene group has superior stability in this context. In addition, it is believed that having some asymmetry to the molecule, i.e., $R_1$, $R_2$, $R_3$ and $R_4$ are not all the same, leads to the formation of better amorphous films.

In OLED operation, some electrons may leak into the hole transport layer due to incomplete hole-electron charge recombination in the emissive layer. If the hole transport material is not stable to reduction, the device lifetime may be shortened. If the hole transport material is stable to reduction, the stability may be enhanced. Triphenylene is a polyaromatic compound which has extended π-conjugation and yet relatively high triplet energy. The benefits of triphenylene compounds, particularly in phosphorescent OLEDs, are further described in US20060280965, which is incorporated by reference in its entirety. For many of the triphenylene containing materials described herein, the hole transport materials retain the hole transporting properties by having the triarylamine moieties. In addition, the triphenylene moiety is believed to provide stabilization toward reduction of the hole transport materials when electrons leak into the hole transporting layer. The advantage of having triphenylene groups are demonstrated in the device examples compared to a hole transporting material α-NPD which contains a 1-naphthyl group as the most conjugated part. It is believed that a naphthyl group does not provide as much reduction stabilization as a triphenylene group, and consequently, triphenylene containing hole transport materials described herein result in more stable OLEDs. Furthermore, such materials result in more efficient OLEDs compared to devices with α-NPD, which may be due to the higher triplet energy of triphenylene as compared to naphthalene.

Preferably, at least one of $R_1$ and $R_3$, and at least one of $R_2$ and $R_4$, is a group that includes a triphenylene group. While molecules having a group with a triphenylene attached to only one nitrogen of the core are useable, it is believed that molecules having at least one group containing a triphenylene attached to each nitrogen of the core, by providing more triphenylenes in more places, results in a more stable molecule. It is also believed that adding additional triphenylenes after there is at least one attached to each nitrogen may not result in much further improvement. While it is generally easier to have all of the triphenylene groups in a molecule be the same group, possible multiple times, different triphenylene groups may also be used in the same molecule.

In addition, it is believed that the use of a phenyl "spacer" affects the triplet energy of the molecule. For example,

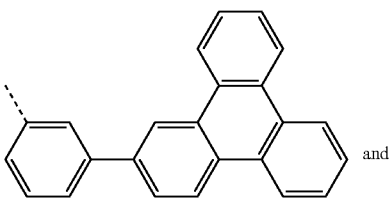

and

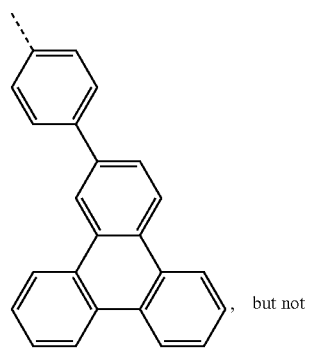

, but not

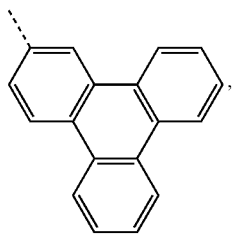

, include a phenyl spacer. Different triplet energies are preferred for different device architectures, and the ability to insert or omit a phenyl spacer gives flexibility in designing devices.

The benzidene core is preferred, i.e., the part of the composition represented by Formula I is more specifically:

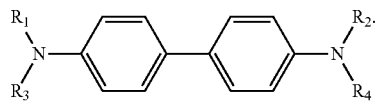
(Formula II)

Molecules including each of the triphenylene-containing groups disclosed herein may be preferred, depending upon the context.

A composition of matter where at least one of $R_1$, $R_2$, $R_3$ and $R_4$ is

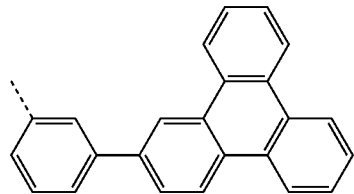
S-2 may be preferred. These compounds may be referred to as being in the A-group of compounds. Non-limiting examples of specific preferred molecules including this substituent include:

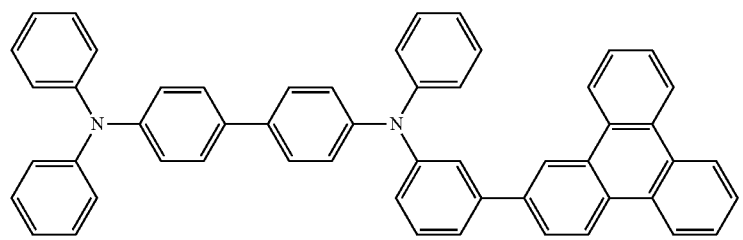
A-1

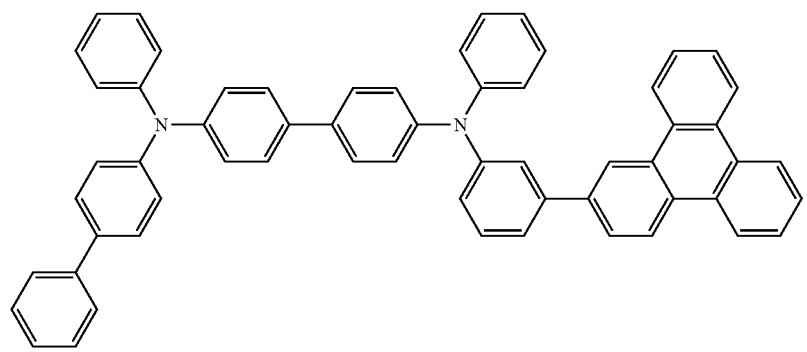
A-2

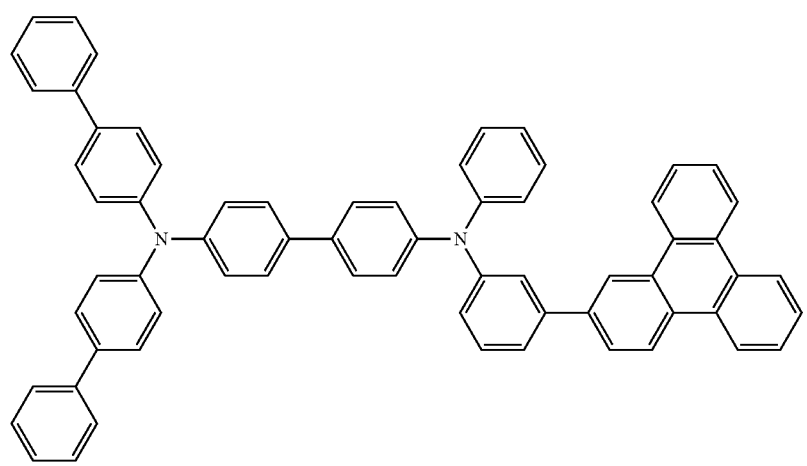
A-3

A-4
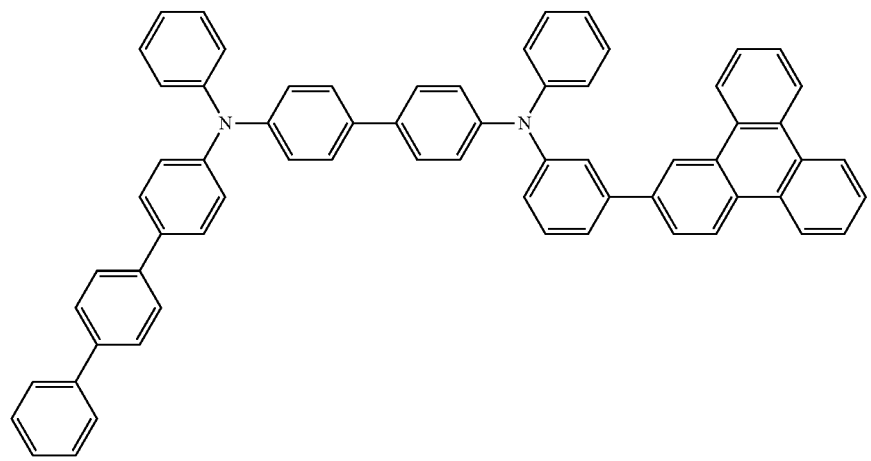
A-5
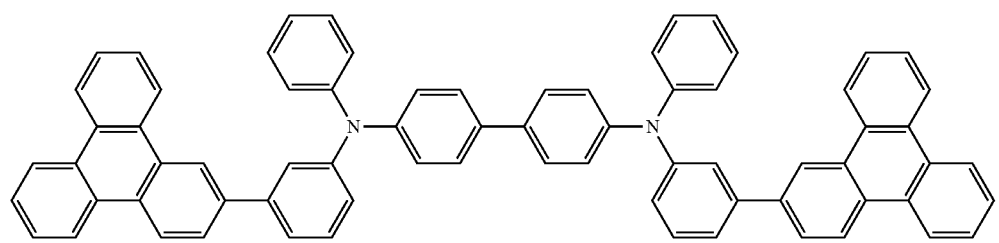
A-6
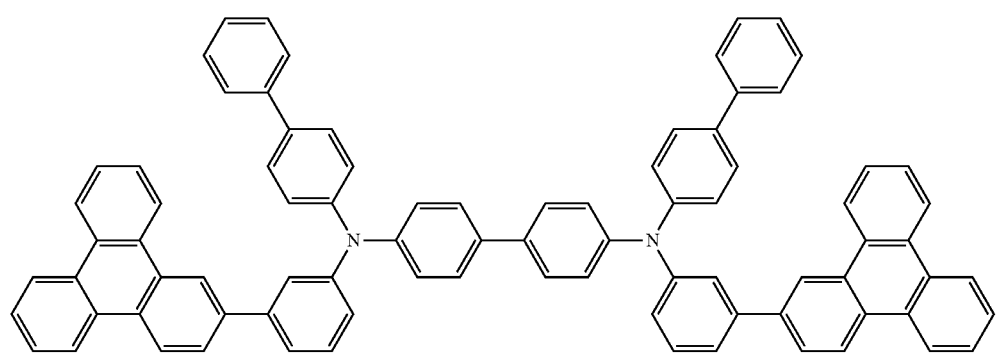

A composition of matter where at least one of $R_1$, $R_2$, $R_3$ and $R_4$ is
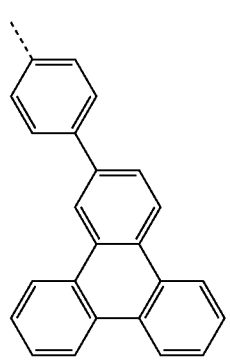
may be preferred. These compounds may be referred to as being in the B-group of compounds. Non-limiting examples of specific preferred molecules including this substituent include:
B-1
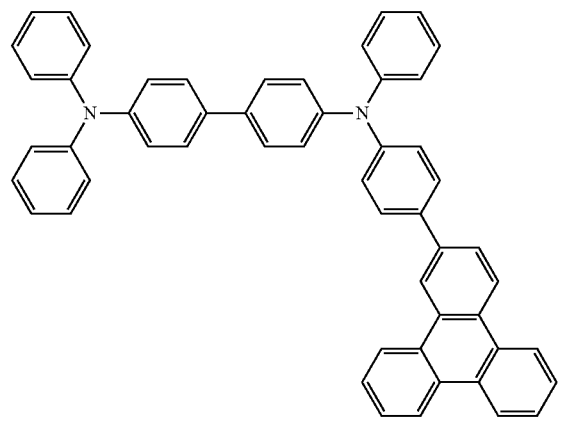
B-2
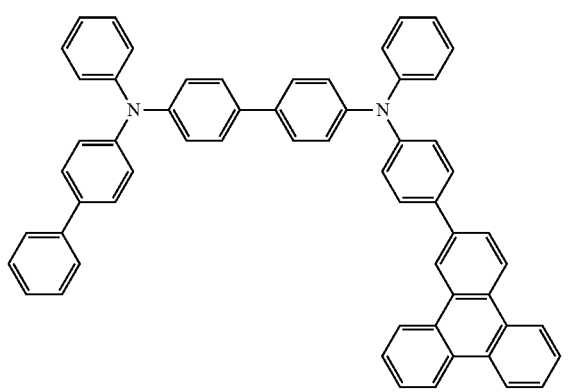
B-3
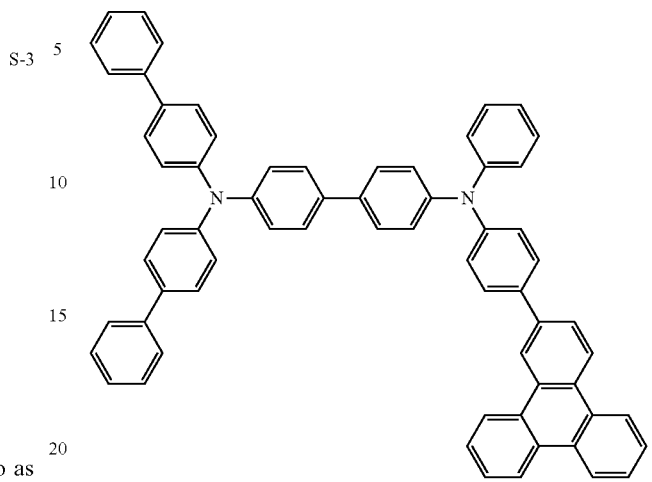
B-4
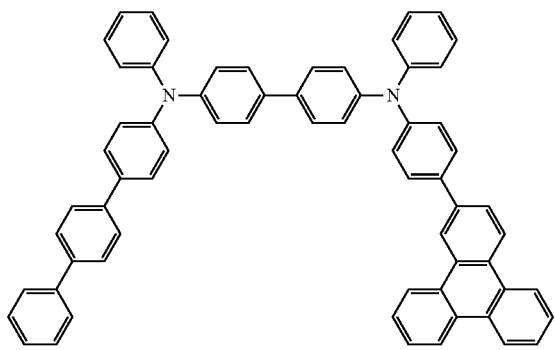
B-5
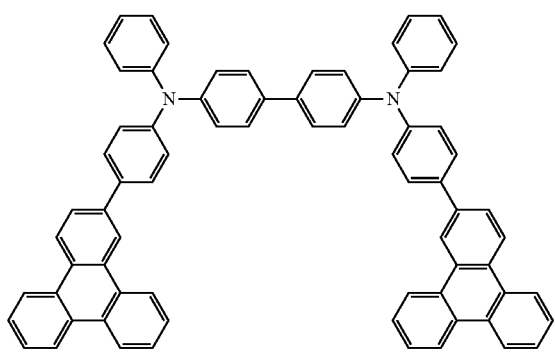

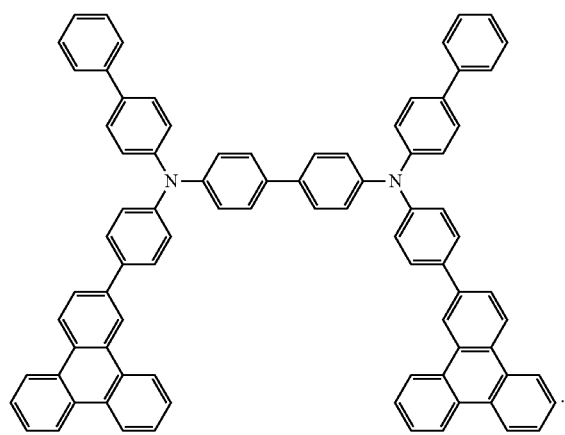
B-6
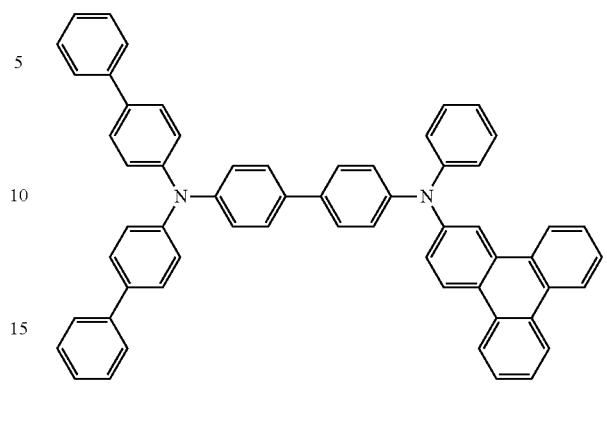
C-3
A composition of matter where at least one of R$_1$, R$_2$, R$_3$ and R$_4$ is
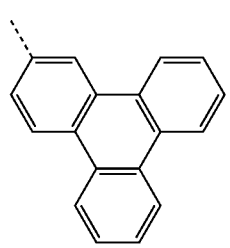
S-4
may be preferred. These compounds may be referred to as being in the C-group of compounds. Non-limiting examples of specific preferred molecules including this substituent include:
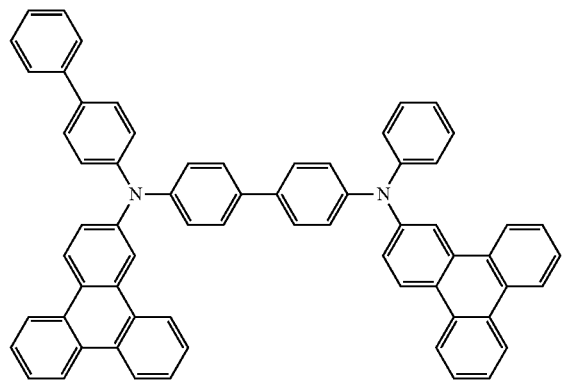
C-4
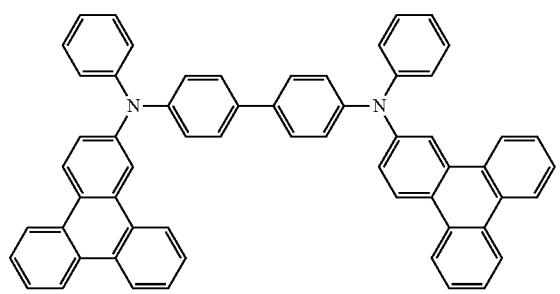
C-1
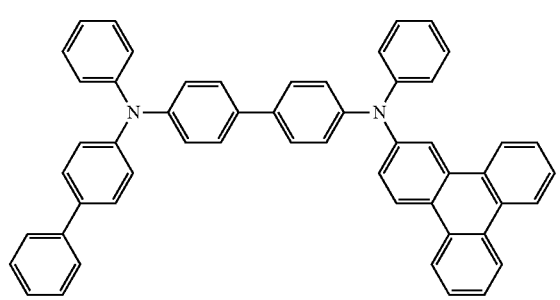
C-2
C-5
C-6

For the R groups that do not include a triphenylene, the following structures are preferred:

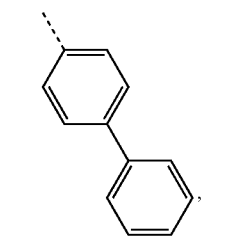
S-5

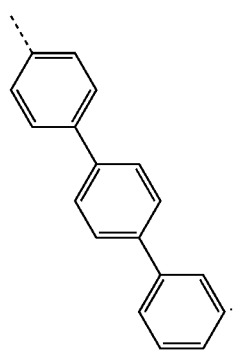
S-6

A composition of matter of Formula I is preferred where each of $R_1$, $R_2$, $R_3$ and $R_4$ is independently selected from the group consisting of:

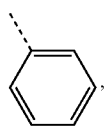
S-1

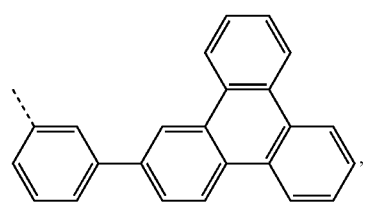
S-2

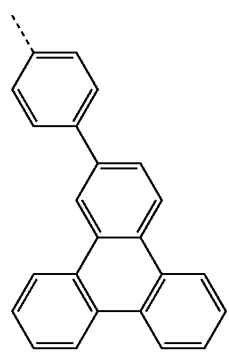
S-3

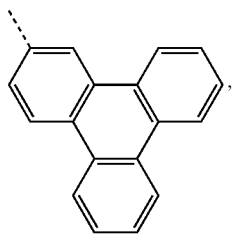
S-4

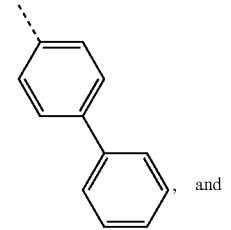
S-5
, and

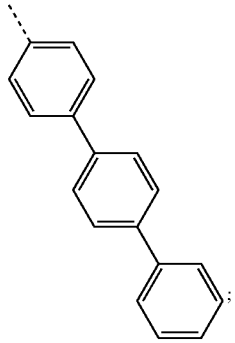
S-6
;

and there are no further substitutions to $R_1$, $R_2$, $R_3$ and $R_4$.

Molecules A-1, A-5 and C-1 have been synthesized, and a description of the synthesis is provided. The other molecules in the A, B and C groups of molecules, and the variations to those molecules described herein, can be readily fabricated using similar chemical synthesis.

An organic light emitting device is also provided. The device may include an anode, a cathode, and an organic emissive layer disposed between the anode and the cathode. The organic emissive layer may includes a host and a phosphorescent dopant. The device may also include an organic hole transport layer comprising a hole transport material, disposed between the organic emissive layer and the anode, and in direct contact with the organic emissive layer. The hole transport layer may have the structure of the novel compositions of matter disclosed herein, i.e., the structure of the novel materials having a core consistent with Formula I. The phosphorescent dopant is preferably an organometallic iridium material.

In addition, consumer products wherein the consumer product includes an organic light emitting device including a composition of matter having the structure of Formula I, as described, are provided. Selections for the substituents and structures described as preferred for the compositions of matter having the structure Formula I are also preferred for the devices and the consumer products including devices that comprise a composition of matter having the structure of Formula I. These selections include those described for substituents $R_1$, $R_2$, $R_3$, and $R_4$, Formula II, and structures A-1 through A-6, B-1 through B-6, and C-1 through C-6.

Organic light emitting devices having at least one of $R_1$, $R_2$, $R_3$ and $R_4$ being:

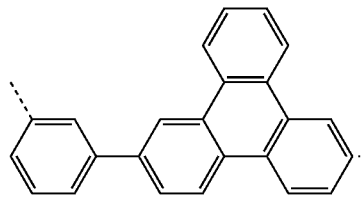

S-2 were fabricated. Specifically, molecule A-1 was used to fabricate devices, and it is believed that other molecules as disclosed herein having the same group would have similar performance. The devices had particularly good performance.

Organic light emitting devices having at least one of $R_1$, $R_2$, $R_3$ and $R_4$ being:

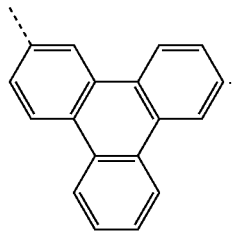

S-4 were fabricated. Specifically molecule C-1 was used to fabricate the device, and it is believed that other molecules as disclosed herein having the same group would have similar performance.

It is believed that the triphenylene-containing compounds disclosed herein, when used as a hole transport layer, work particularly well in devices where the host is a compound comprising a triphenylene containing benzo-fused thiophene. Devices fabricated with this combination showed particularly good performance. Such hosts are disclosed in U.S. Patent Application 61/013,391, filed Dec. 28, 2007, inventor Ma, Bin, which is incorporated herein by reference in its entirety and particularly for claimed subject matter. The C group of compounds are preferred hole transport materials for this combination. Compound 3 is a preferred example of such a host.

It is believed that the triphenylene-containing compounds disclosed herein, when used as a hole transport layer, work particularly well in devices where the host is an aryltriphenylene compound. Such hosts are disclosed in U.S. Patent Publication 2006-0280965, filed May 31, 2006, inventors Kwong et al., which is incorporated herein by reference in its entirety and particularly for claimed subject matter. The C group of compounds are preferred hole transport materials for this combination. Compound 2 is a preferred example of such a host.

It is believed that triphenylene containing hole transport materials described herein are desirable for use in fluorescent OLEDs in addition to phosphorescent OLEDs.

As used herein, the following compounds have the following structures:

Compound 1—disclosed in JP 2000-299497:

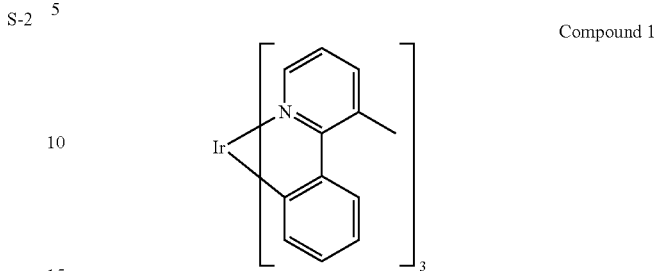

Compound 1

Compound 2—disclosed in U.S. Patent Publication 2006-0280965, inventors Kwong et. al, filed May 31, 2006:

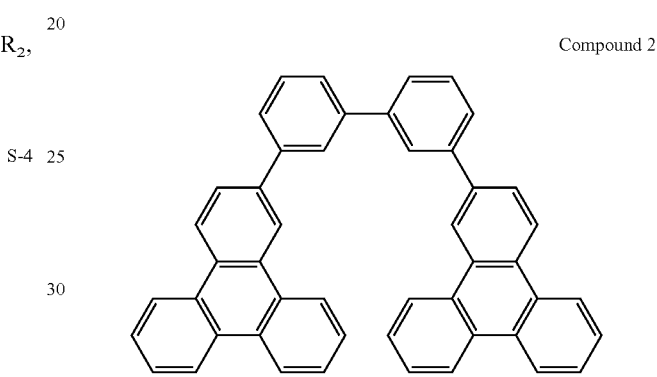

Compound 2

Compound 3—disclosed in U.S. Patent Application 61/013,391, filed Dec. 28, 2007, inventor Ma, Bin.

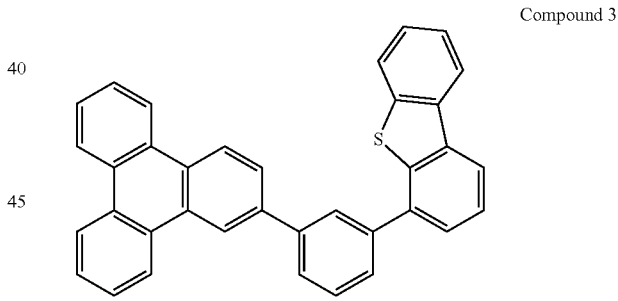

Compound 3

Compound 4—red phosphorescent emitter disclosed in U.S. patent application Ser. No. 12/044,234, filed Mar. 7, 2008, inventors Kwong et al.

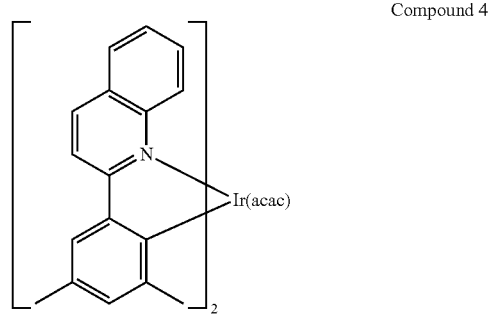

Compound 4

Bis(2-methyl-8-hydroxyquinolinolato) (4-phenylphenolato) aluminum (BAlq) and tris-(8-hydroxyquinolato) aluminum (Alq$_3$) are well known materials. LG-101 and LG-201 are proprietary materials available for purchase from LG Chem, Inc. of Korea.

EXPERIMENTAL

Synthesis of A-1

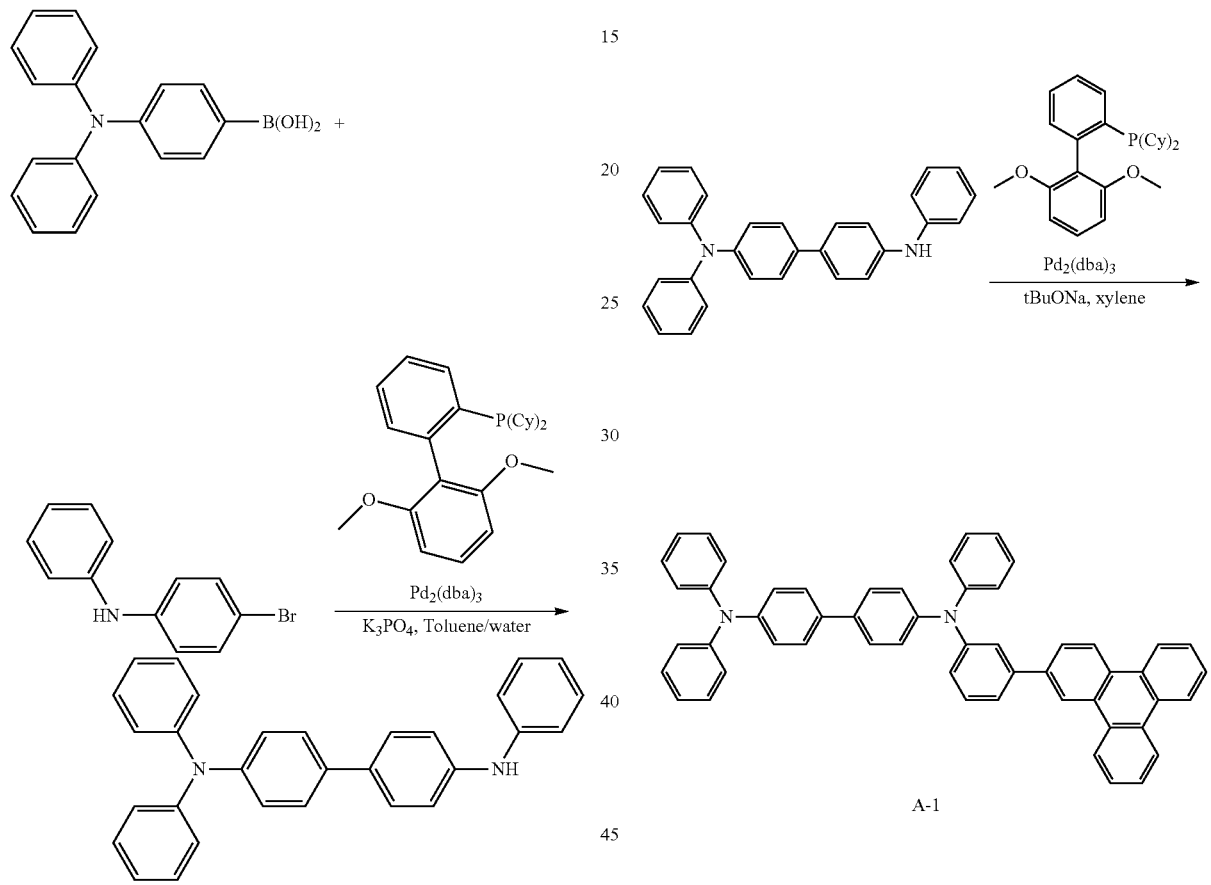

Synthesis of A-1

Synthesis of N$^4$,N$^4$,N$^{4'}$-triphenylbiphenyl-4,4'-diamine 4-(diphenylamino)phenylboronic acid (4.87 g, 16.8 mmol), 4-bromo-N-phenylaniline (3.5 g, 14 mmol), potassium phosphate (9.2 g, 42 mmol), dicyclohexyl(2',6'-dimethoxybiphenyl-2-yl)phosphine (0.23 g, 0.56 mmol) were added to a three-neck flask under nitrogen. 200 mL of toluene and 20 mL of water was then added. The solution was degassed with nitrogen for 20 minutes. Pd$_2$(dba)$_3$ (0.13 g, 0.14 mmol) was added to the mixture. The mixture was then heated up to reflux overnight. After cooled to room temperature, the organic layer was separated and dried over magnesium sulfate. After evaporating solvent, the residue was purified by column chromatography using 1:2 dichloromethane and hexanes as eluent. 4.7 g of desired product was obtained. (81% yield)

N$^4$,N$^4$,N$^{4'}$-triphenyl-N$^{4'}$-(3-(triphenylen-2-yl)phenyl)biphenyl-4,4'-diamine Pd$_2$(dba)$_3$ (0.07 g, 0.07 mmol) and dicyclohexyl(2',6'-dimethoxybiphenyl-2-yl)phosphine (0.13 g, 0.3 mmol) were added to a three-neck flask under nitrogen. 150 mL of xylene was then added. The solution was stirred under nitrogen for 20 minutes. To the solution was added 3-(triphenylen-2-yl)phenyl trifluoromethanesulfonate (3.87 g, 8.5 mmol), sodium tert-butoxide (1.1 g, 11.6 mmol), and N$^4$,N$^4$,N$^{4'}$-triphenylbiphenyl-4,4'-diamine (3.2 g, 7.7 mmol) in sequence. The mixture was then heated up to reflux overnight. After cooled to room temperature, 300 mL of dichloromethane was added to the solution. The solution was then filtered through a celite bed. After evaporating solvent, the residue was purified by column chromatography using 1:3 dichloromethane and hexanes as eluent. 3.5 g of desired product was obtained after purification. The product was further purified by high vacuum sublimation. (64% yield)

Synthesis of A-5

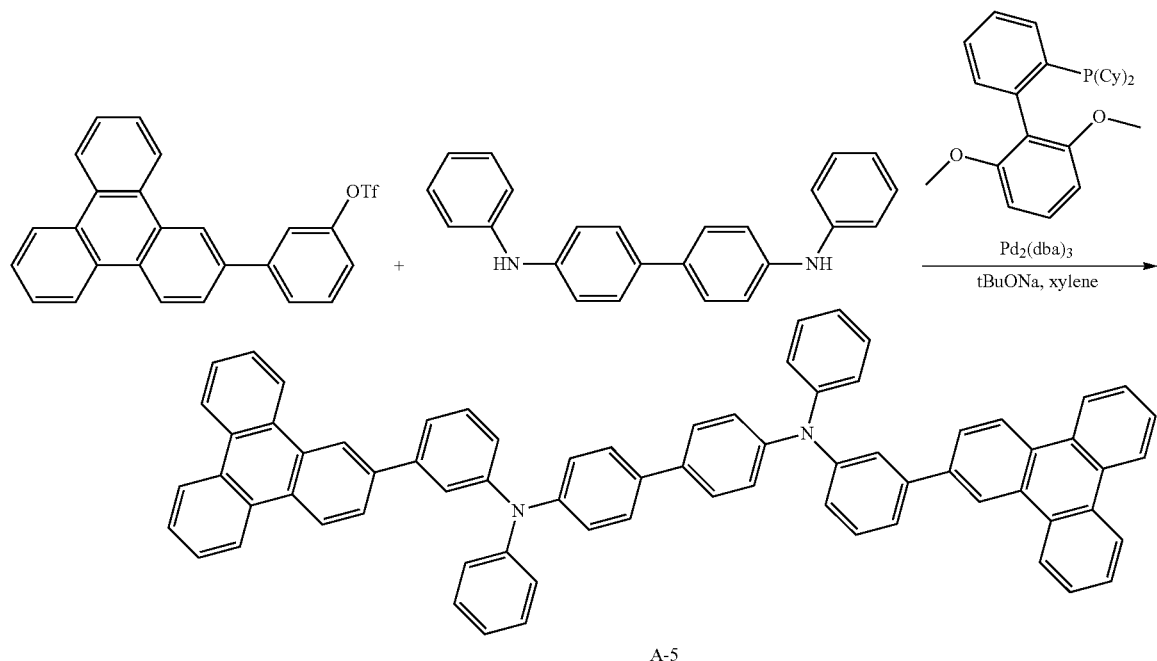

A-5

Synthesis of A-5

N⁴,N⁴'-diphenyl-N⁴,N⁴'-bis(3-(triphenylen-2-yl)phenyl) biphenyl-4,4'-diamine Pd$_2$(dba)$_3$ (0.1 g, 0.1 mmol) and dicyclohexyl(2',6'-dimethoxybiphenyl-2-yl)phosphine (0.17 g, 0.4 mmol) were added to a three-neck flask under nitrogen. 150 mL of xylene was then added. The solution was stirred under nitrogen for 20 minutes. To the solution was added 3-(triphenylen-2-yl)phenyl trifluoromethanesulfonate (5.0 g, 11.1 mmol), sodium tert-butoxide (1.5 g, 15 mmol), and N⁴,N⁴'-diphenylbiphenyl-4,4'-diamine (1.7 g, 5 mmol) in sequence. The mixture was then heated up to reflux overnight. After cooled to room temperature, the mixture precipitated from 300 mL of methanol. Solid was collected by filtration. The solid was then redissolved in dichloromethane and dried over magnesium sulfate. After evaporating solvent, 4.4 g of desired product was obtained. The compound was further purified by high vacuum sublimation.

Synthesis of C-1

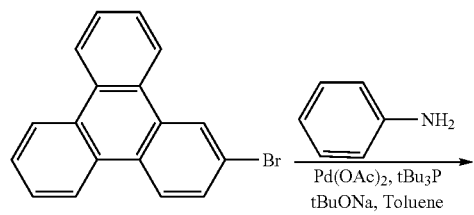

-continued

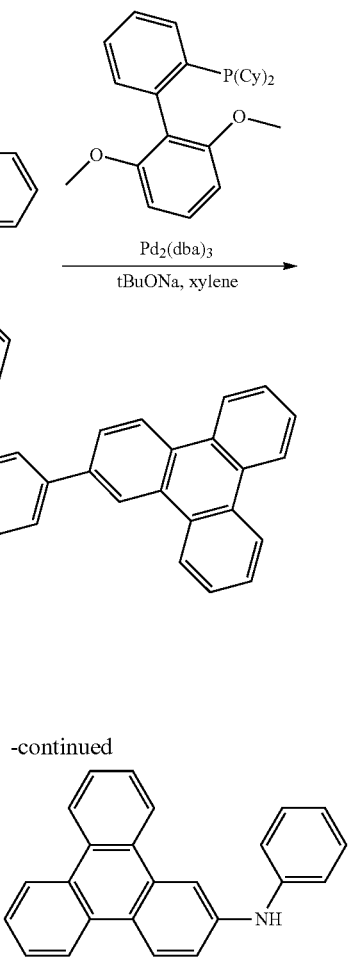

Synthesis of N-phenyltriphenylen-2-amine

Palladium acetate (0.01 g, 0.06 mmol) and 1.0 M tri(t-butyl)phosphine solution in toluene (0.02 mL, 0.02 mmol) were added to a three-neck flask under nitrogen. 100 mL of toluene was then added. The solution was stirred under nitrogen until the color disappeared. To the solution was added 2-bromotriphenylene (2 g, 6.5 mmol), sodium tert-butoxide (0.94 g, 9.8 mmol), and aniline (1.8 g, 20 mmol) in sequence. The mixture was then heated up to reflux overnight. After cooled to room temperature, the mixture was filtered through a celite bed and washed thoroughly with dichloromethane. The product was purified by column chromatography using 1:7 dichloromethane and hexanes as eluent. 0.8 g of desired product was obtained after purification.

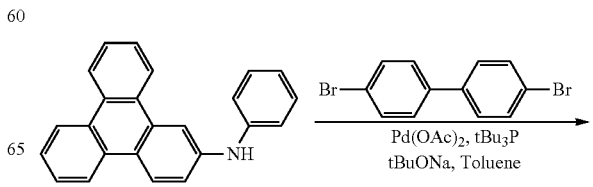

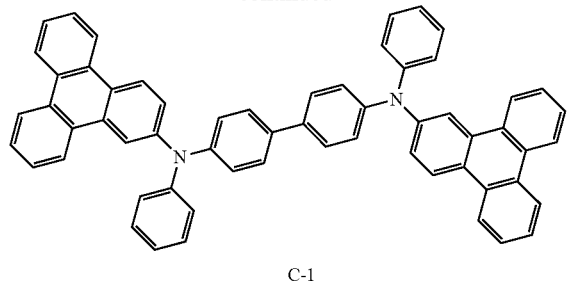

C-1

Synthesis of C-1

$N^4,N^{4'}$-diphenyl-$N^4,N^{4'}$-di(triphenylen-2-yl)biphenyl-4,4'-diamine palladium acetate (0.2 mg, 0.03 mmol) and 1.0 M tri(t-butyl)phosphine solution in toluene (0.1 mL, 0.1 mmol) were added to a three-neck flask under nitrogen. 60 mL of xylene was then added. The solution was stirred under nitrogen until the color disappeared. To the solution was added 4,4'-dibrombiphenyl (0.33 g, 1 mmol), sodium tert-butoxide (0.3 g, 3 mmol), and N-phenyltriphenylen-2-amine (0.7 g, 2.2 mmol) in sequence. The mixture was then heated up to reflux overnight. After cooled to room temperature, the mixture was filtered through a celite bed and washed thoroughly with dichloromethane. The product was purified by column chromatography using 1:2 dichloromethane and hexanes as eluent. 0.4 g of desired product was obtained after purification. The product was further purified by high vacuum sublimation.

Devices

Devices were fabricated using standard techniques. The devices have structures similar to that shown in FIG. 1, but including the specific layers and materials described in the tables. Cmpd. is an abbreviation of compound. Ex. is an abbreviation of Example.

TABLE 1

Structures of green PHOLEDs with novel HTL materials and novel host/HTL combinations vs. comparative examples.

| Ex. | HIL | HTL | Host | Cmpd. 1, % | BL | ETL |
|---|---|---|---|---|---|---|
| 1 | Cmpd 1 100 Å | -NPD 300 Å | Cmpd 2 | 10% | Cmpd 2 100 Å | Alq$_3$ 400 Å |
| 2 | Cmpd 1 100 Å | C-1 300 Å | Cmpd 2 | 10% | Cmpd 2 100 Å | Alq$_3$ 400 Å |
| 3 | LG-101 300 Å | -NPD 100 Å | Cmpd 3 | 10% | Cmpd 3 100 Å | LG-201 300 Å |
| 4 | LG-101 300 Å | C-1 100 Å | Cmpd 3 | 10% | Cmpd 3 100 Å | LG-201 300 Å |
| 5 | LG-101 300 Å | -NPD 100 Å | Cmpd 3 | 10% | Cmpd 3 100 Å | Alq$_3$ 400 Å |
| 6 | LG-101 300 Å | C-1 100 Å | Cmpd 3 | 10% | Cmpd 3 100 Å | Alq$_3$ 400 Å |

TABLE 2

Performance of green PHOLEDs with novel HTL materials and novel host/HTL combinations vs comparative examples.

| | At 1,000 nits | | | | | | At 40 mA/cm² LT$_{80\%}$ [h] | | |
|---|---|---|---|---|---|---|---|---|---|
| | CIE | | Voltage | LE | EQE | PE | LT$_{50\%}$ | Lo | | |
| Ex. | x | y | [V] | [cd/A] | [%] | [lm/W] | [h] | [cd/m²] | RT | 70° C. |
| 1 | 0.364 | 0.603 | 6.4 | 58.4 | 16.0 | 28.7 | | 16,450 | 233 | 19 |
| 2 | 0.367 | 0.601 | 6.1 | 62.9 | 17.3 | 32.4 | | 18,100 | 359 | 29 |
| 3 | 0.351 | 0.608 | 5.6 | 49.1 | 13.5 | 27.5 | 204,995 | 14,624 | 349 | 65 |
| 4 | 0.356 | 0.605 | 5.5 | 53.5 | 14.7 | 30.5 | 428,521 | 17,280 | 359 | 76 |
| 5 | 0.351 | 0.612 | 5.8 | 53.5 | 14.7 | 29.0 | 213,955 | 16,084 | 372 | |
| 6 | 0.355 | 0.609 | 5.7 | 59.1 | 16.3 | 32.6 | 434,086 | 18,875 | 350 | |

3 groups of experiments are shown in tables 1 and 2. The superior performance of green PHOLED devices with novel HTL material C-1 is shown relative to devices having an NPD HTL. The desirability of combining HTL materials similar to C-1 with hosts similar to Compounds 2 and 3 is also shown.

Group 1

Examples 1 and 2

The difference between Example 1 (comparative) and Example 2 is that Example 1 has an α-NPD HTL, whereas Example 2 has an HTL of compound C-1. The combination of HTL C-1 with Compound 2 as a host gives results superior to a similar device using an α-NPD HTL. Example 2 shows superior performance in device voltage, luminous efficiency and the lifetime. Moreover, the results for Example 2 are particularly good for a green-emitting device in general, showing the desirability of combining HTLs with compounds similar to C-1 with hosts similar to Compound 2.

Group 2

Examples 3 and 4

The difference between Example 3 (comparative) and Example 4 is that Example 3 has an α-NPD HTL, whereas Example 4 has an HTL of Compound C-1. There is also a difference in the hole injection layer (HIL). The combination of HTL C-1 with Compound 3 as a host gives results superior to a similar device using an α-NPD HTL. Example 4 shows superior performance in efficiency and the lifetime. Moreover, the results for Example 4 are particularly good for a green-emitting device in general, showing the desirability of combining HTLs with compounds similar to C-1 with hosts similar to Compound 3.

Group 3

Examples 5 and 6

Group 3 makes a similar comparison to that made in Group 2, except using an ETL of $Alq_3$ instead of LG-201. The same conclusions can be drawn from Group 3 as from Group 2.

TABLE 3

Structures of red PHOLEDs with novel HTL materials

| Ex. | HIL | HTL | Host | Cmpd 4, % | BL | ETL |
|---|---|---|---|---|---|---|
| 7 | Cmpd 1 100 Å | NPD 400 Å | BAlq | 9% | none | $Alq_3$ 550 Å |
| 8 | Cmpd 1 100 Å | C-1 400 Å | BAlq | 9% | none | $Alq_3$ 550 Å |
| 9 | Cmpd 1 100 Å | A-1 400 Å | BAlq | 9% | none | $Alq_3$ 550 Å |
| 10 | LG-101 400 Å | NPD 100 Å | BAlq | 9% | none | $Alq_3$ 550 Å |
| 11 | LG-101 400 Å | C-1 100 Å | BAlq | 9% | none | $Alq_3$ 550 Å |
| 12 | LG-101 400 Å | A-1 100 Å | BAlq | 9% | none | $Alq_3$ 550 Å |

TABLE 4

Performance of red PHOLEDs with novel HTL materials

| | CIE | | At 1,000 nits | | | | At 40 mA/cm$^2$ $LT_{80\%}$ [h] | |
|---|---|---|---|---|---|---|---|---|
| Ex. | x | y | Voltage [V] | LE [cd/A] | EQE [%] | PE [lm/W] | Lo [cd/m$^2$] RT | 70° C. |
| 7 | 0.667 | 0.331 | 8.2 | 20.0 | 18.9 | 7.7 | 6,439  850 | 90 |
| 8 | 0.667 | 0.331 | 8.0 | 18.5 | 17.8 | 7.3 | 6,086  600 | 83 |
| 9 | 0.666 | 0.332 | 8.9 | 19.9 | 18.7 | 7.0 | 6,220  297 | |
| 10 | 0.666 | 0.332 | 7.0 | 14.4 | 13.4 | 6.5 | 4,420 1,000 | |
| 11 | 0.666 | 0.332 | 7.1 | 14.9 | 14.0 | 6.6 | 4,643  860 | |
| 12 | 0.666 | 0.332 | 7.2 | 16.5 | 15.4 | 7.2 | 5,273  540 | |

2 groups of experiments are shown in tables 3 and 4. The performance of red PHOLED devices with novel HTL materials C-1 and A-1 is shown relative to devices having an α-NPD HTL. A BAlq host is used for all devices.

Group 4

Examples 7, 8 and 9

The difference between Example 7 (comparative) and Examples 8 and 9 is that Example 7 has an NPD HTL, whereas Examples 8 and 9 have an HTLs of compound C-1 and A-1, respectively. All HTLs are shown in combination with BAlq host. Examples 8 and 9 reveal performance lower in terms of efficiency and lifetime vs. α-NPD HTL comparative example 7. However, the performance of the devices of Examples 8 and 9 are still well above what is needed for a commercial device.

Group 5

Examples 10, 11 and 12

Group 5 makes a similar comparison to that made in Group 4, except using an HIL of LG-101 instead of Compound 1. The same conclusions can be drawn from Group 5 as from Group 4.

For red devices, the results for the devices using C-1 and A-1 as an HTL are not necessarily superior to those using NPD. But, all of the devices in tables 3 and 4 show performance well above that needed for a commercial display.

As a result, the suitability of HTL materials similar to C-1 and A-1 for a common device architecture is shown. It is desirable in many manufacturing scenarios to use the same materials in different devices as much as possible. For devices emitting different colors, such as red and green, the emissive molecule may be different. But it is still desirable that the red and green devices use the same non-emissive materials, such as the HTL, to as large an extent as possible.

In addition, green PHOLED lifetime is more of a limiting factor for commercialization than red PHOLED lifetime. Red PHOLEDs with any HTL have typically good performance (lifetime), enough for the mass production. Thus, an HTL material that exhibits superior performance in a green device is highly desirable, even if the material has lower performance in a red device.

A comparison of Groups 1, 2 and 3 with Groups 4 and 5 also shows that, while compounds similar to A-1 and C-1 can be used in different device architectures, those architectures having a combination of compounds similar to A-1 and C-1 in the HTL with certain hosts, such as those similar to Compound 2 and Compound 3, are particularly desirable and lead to unexpectedly good device performance.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 5 below. Table 5 lists non-limiting classes of materials, non-limiting examples of compounds for each class, and references that disclose the materials.

TABLE 5

| MATERIAL | EXAMPLES OF MATERIAL | PUBLICATIONS |
|---|---|---|
| Hole injection materials | | |
| Phthalocyanine and porphryin compounds | 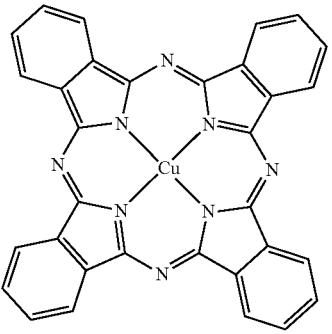 | Appl. Phys. Lett. 69, 2160 (1996) |
| Starburst triarylamines | 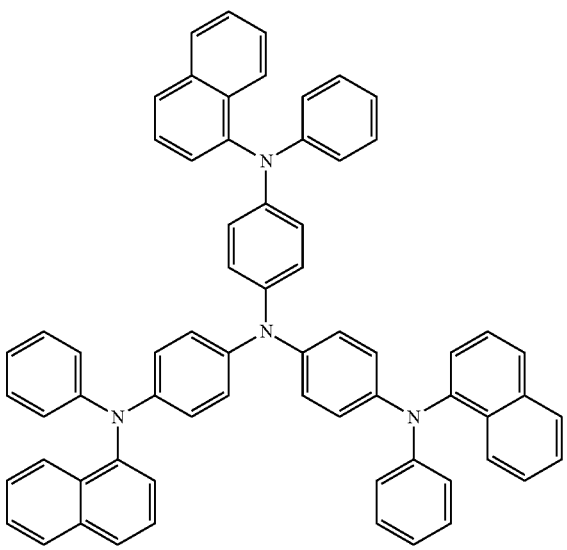 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |

TABLE 5-continued

| MATERIAL | EXAMPLES OF MATERIAL | PUBLICATIONS |
| --- | --- | --- |
| CF$_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) |
| Arylamines complexed with metal oxides such as molybdenum and tungsten oxides | + MoO$_x$ | SID Symposium Digest, 37, 923 (2006) |
| Hole transporting materials | | |
| Triarylamines (e.g., TPD, α-NPD) | | Appl. Phys. Lett. 51, 913 (1987) |
| | | US5061569 |
| | | EP650955 |

TABLE 5-continued

| MATERIAL | EXAMPLES OF MATERIAL | PUBLICATIONS |
|---|---|---|
|  |  | J. Mater. Chem. 3, 319 (1993) |
|  |  | Appl. Phys. Lett. 90, 183503 (2007) |
|  |  | Appl. Phys. Lett. 90, 183503 (2007) |
| Triaylamine on spirofluorene core |  | Synth. Met. 91, 209 (1997) |

TABLE 5-continued
| MATERIAL | EXAMPLES OF MATERIAL | PUBLICATIONS |
|---|---|---|
| Arylamine carbazole compounds | 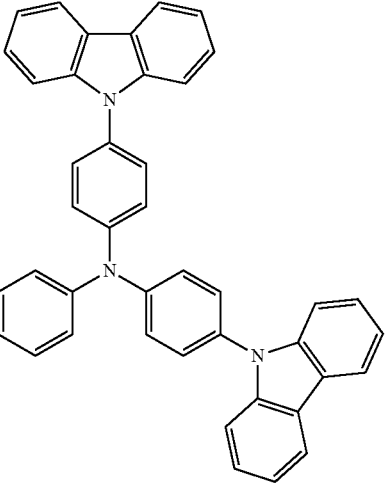 | Adv. Mater. 6, 677 (1994) |
| Indolocarbazoles | 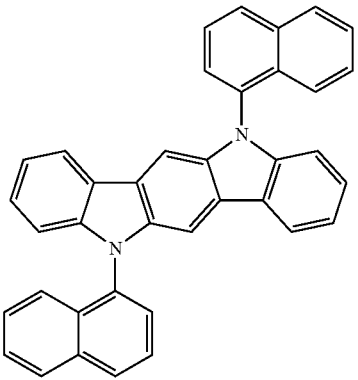 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 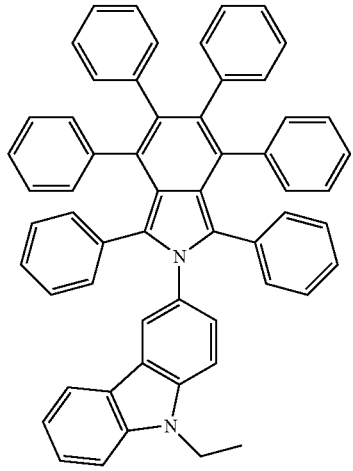 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
Phosphorescent OLED host materials
Red hosts TABLE 5-continued
| MATERIAL | EXAMPLES OF MATERIAL | PUBLICATIONS |
|---|---|---|
| Arylcarbazoles | 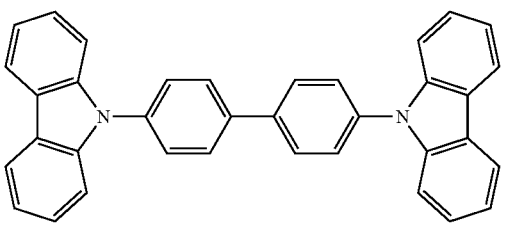 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 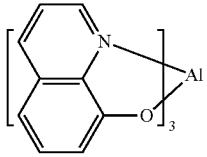 | Nature 395, 151 (1998) |
| | 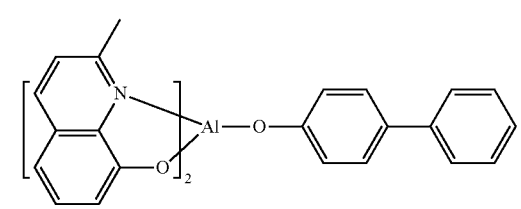 | US20060202194 |
| | 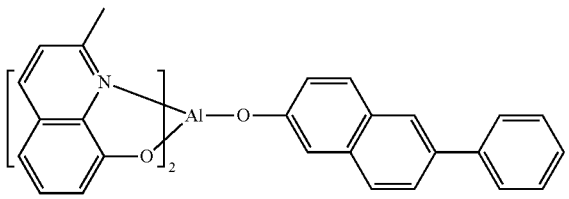 | WO2005014551 |
| Metal phenoxybenzothiazole compounds | 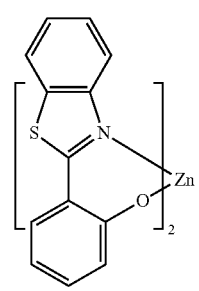 | Appl. Phys. Lett. 90, 123509 (2007) |
| Conjugated oligomers and polymers (e.g., polyfluorene) | 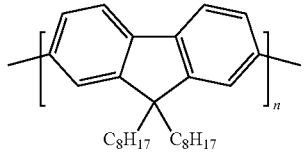 | Org. Electron. 1, 15 (2000) |
| Green hosts | | |
| Arylcarbazoles | 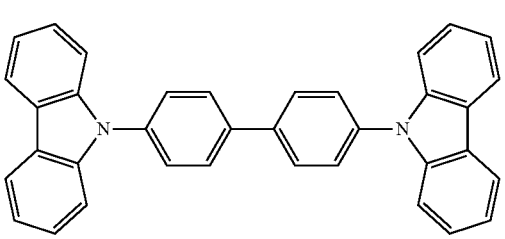 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 5-continued

| MATERIAL | EXAMPLES OF MATERIAL | PUBLICATIONS |
|---|---|---|
| | | US2003175553 |
| | | WO2001039234 |
| Aryltriphenylene compounds | | US20060280965 |
| | | US20060280965 |
| Polymers (e.g., PVK) | | Appl. Phys. Lett. 77, 2280 (2000) |
| Spirofluorene compounds | | WO2004093207 |

TABLE 5-continued

| MATERIAL | EXAMPLES OF MATERIAL | PUBLICATIONS |
|---|---|---|
| Metal phenoxy-benzooxazole compounds | | WO05089025 |
| | | WO06132173 |
| | | JP200511610 |
| Spirofluorene-carbazole compounds | | JP2007254297 |
| | | JP2007254297 |

TABLE 5-continued

| MATERIAL | EXAMPLES OF MATERIAL | PUBLICATIONS |
| --- | --- | --- |
| Indolocabazoles | | WO07063796 |
| | | WO07063754 |
| 5-member ring electron deficient heterocycles (e.g., triazole, oxadiazole) | | J. Appl. Phys. 90, 5048 (2001) |
| | | WO04107822 |
| Metal phenoxypyridine compounds | | WO05030900 |

Blue hosts

| | | |
| --- | --- | --- |
| Arylcarbazoles | | Appl. Phys. Lett, 82, 2422 (2003) |

TABLE 5-continued

| MATERIAL | EXAMPLES OF MATERIAL | PUBLICATIONS |
| --- | --- | --- |
| | | US20070190359 |
| Dibenzothiophene-carbazole compounds | | WO2006114966 |

Phosphorescent dopants
Red dopants

| Heavy metal porphyrins (e.g., PtOEP) | | Nature 395, 151 (1998) |
| --- | --- | --- |
| Iridium(III) organometallic complexes | | Appl. Phys. Lett. 78, 1622 (2001) |
| | | US06835469 |

TABLE 5-continued
| MATERIAL | EXAMPLES OF MATERIAL | PUBLICATIONS |
|---|---|---|
| | 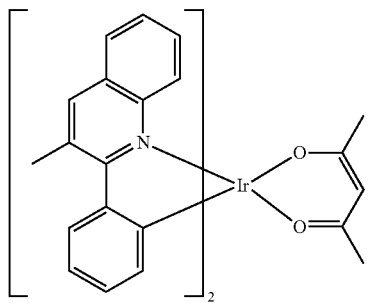 | US06835469 |
| | 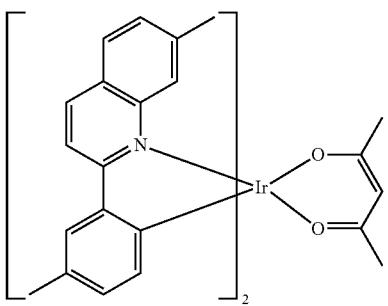 | US20060202194 |
| | 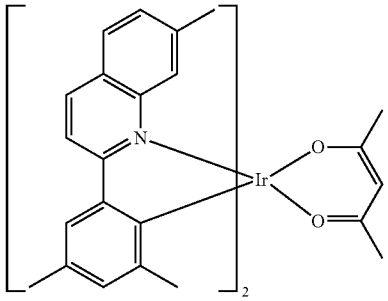 | US20060202194 |
| | 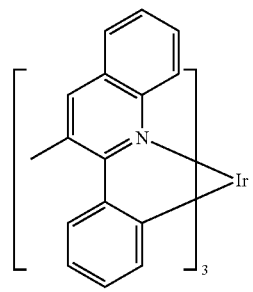 | US07087321 |
| | 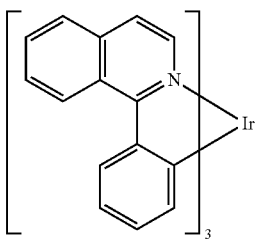 | US07087321 |

TABLE 5-continued
| MATERIAL | EXAMPLES OF MATERIAL | PUBLICATIONS |
|---|---|---|
| | 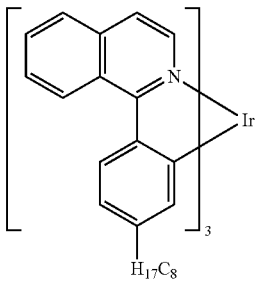 | Adv. Mater. 19, 739 (2007) |
| Platinum(II) organometallic complexes | 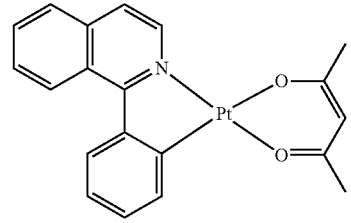 | WO2003040257 |
| Osminum(III) complexes | 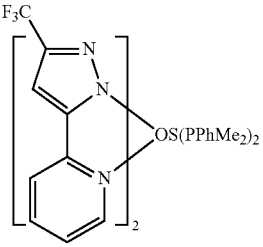 | Chem. Mater. 17, 3532 (2005) |
| Ruthenium(II) complexes | 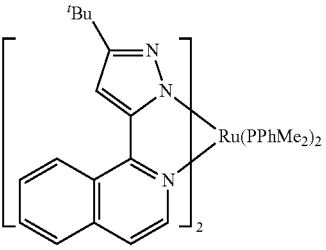 | Adv. Mater. 17, 1059 (2005) |
Green dopants
| | | |
|---|---|---|
| Iridium(III) organometallic complexes | 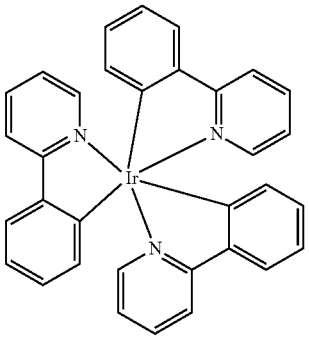<br>and its derivatives | Inorg. Chem. 40, 1704 (2001) |

TABLE 5-continued
| MATERIAL | EXAMPLES OF MATERIAL | PUBLICATIONS |
|---|---|---|
| | 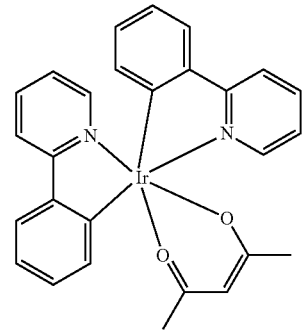 | US2002034656 |
| | 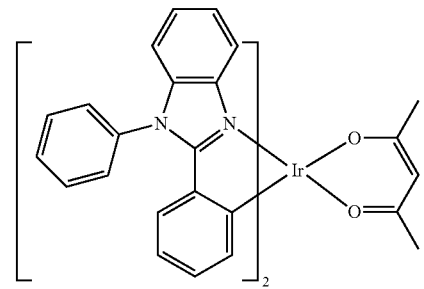 | US06687266 |
| | 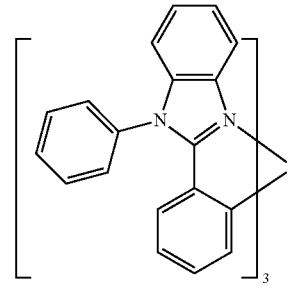 | Chem. Mater. 16, 2480 (2004) |
| | 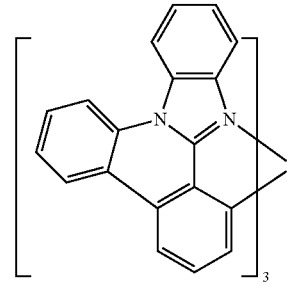 | US2007190359 |
| | 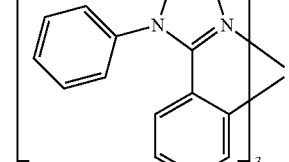 | US 2006008670<br>JP2007123392 |

TABLE 5-continued
| MATERIAL | EXAMPLES OF MATERIAL | PUBLICATIONS |
|---|---|---|
| | 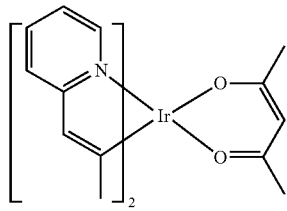 | Adv. Mater. 16, 2003 (2004) |
| | 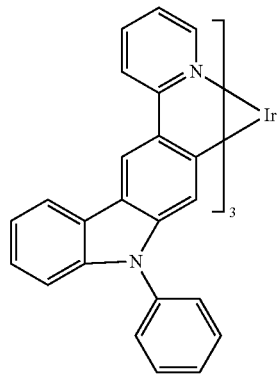 | Angew. Chem. Int. Ed. 2006, 45, 7800 |
| Pt(II) organometallic complexes | 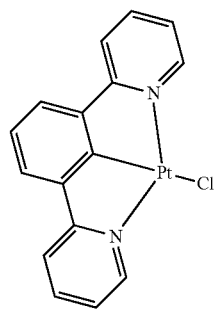 | Appl. Phys. Lett. 86, 153505 (2005) |
| | 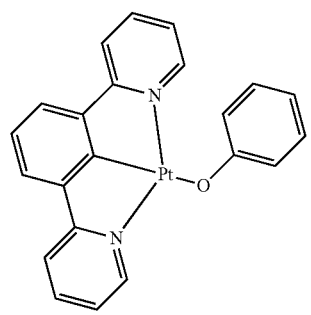 | Appl. Phys. Lett. 86, 153505 (2005) |
| | 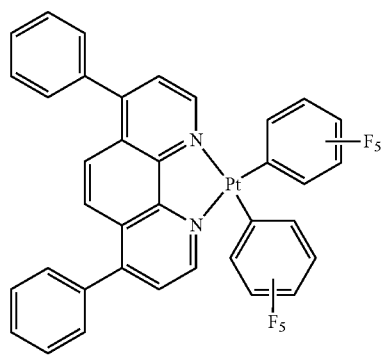 | Chem. Lett. 34, 592 (2005) |

TABLE 5-continued
| MATERIAL | EXAMPLES OF MATERIAL | PUBLICATIONS |
|---|---|---|
| Gold complexes | 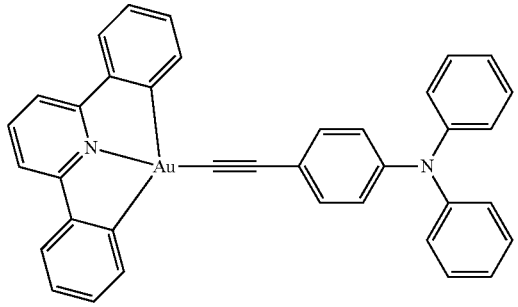 | Chem. Commun. 2906 (2005) |
| Rhenium(III) complexes | 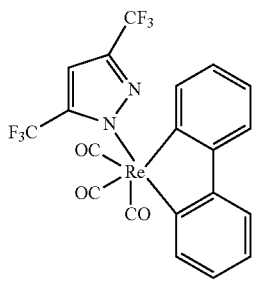 | Inorg. Chem. 42, 1248 (2003) |
Blue dopants
| | | |
|---|---|---|
| Iridium(III) organometallic complexes | 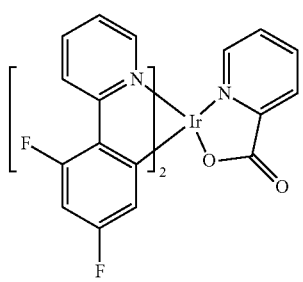 | WO2002002714 |
| | 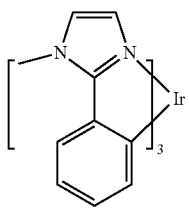 | WO2006009024 |
| | 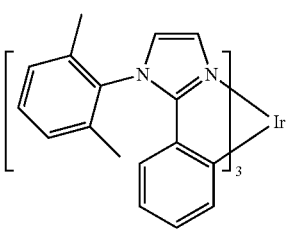 | US2006251923 |

TABLE 5-continued

| MATERIAL | EXAMPLES OF MATERIAL | PUBLICATIONS |
|---|---|---|
| | | WO2006056418, US2005260441 |
| | | US2007190359 |
| | | US2002134984 |
| | | Angew. Chem. Int. Ed. 47, 1 (2008) |
| | | Chem. Mater. 18, 5119 (2006) |
| | | Inorg. Chem. 46, 4308 (2007) |

TABLE 5-continued

| MATERIAL | EXAMPLES OF MATERIAL | PUBLICATIONS |
|---|---|---|
| | | WO05123873 |
| | | WO05123873 |
| | | WO07004380 |
| | | WO06082742 |
| Osmium(II) complexes | | US2005260449 |

TABLE 5-continued

| MATERIAL | EXAMPLES OF MATERIAL | PUBLICATIONS |
| --- | --- | --- |
| | | Organometallics 23, 3745 (2004) |
| Gold complexes | | Appl. Phys. Lett. 74, 1361 (1999) |
| Platinum(II) complexes | | WO06098120, WO06103874 |

Exciton/hole blocking layer materials

| MATERIAL | EXAMPLES OF MATERIAL | PUBLICATIONS |
| --- | --- | --- |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE 5-continued

| MATERIAL | EXAMPLES OF MATERIAL | PUBLICATIONS |
|---|---|---|
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

Electron transporting materials

TABLE 5-continued

| MATERIAL | EXAMPLES OF MATERIAL | PUBLICATIONS |
| --- | --- | --- |
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., Alq$_3$) | | Appl. Phys. Lett. 51, 913 (1987) |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 5-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 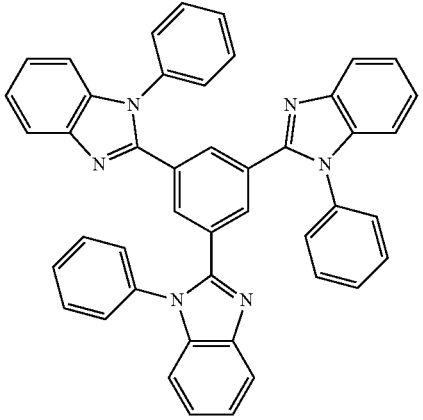 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 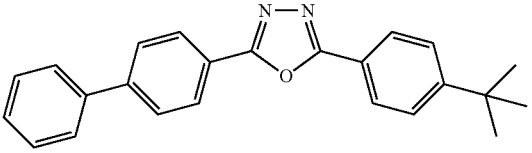 [SMILES: CC(C)(C)c1ccc(-c2nnc(-c3ccc(-c4ccccc4)cc3)o2)cc1] | Appl. Phys. Lett. 55, 1489 (1989) |
| | 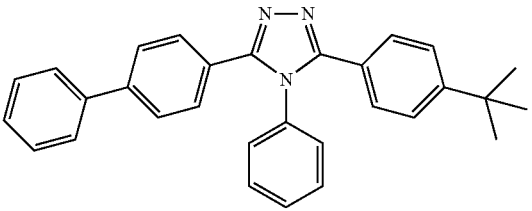 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 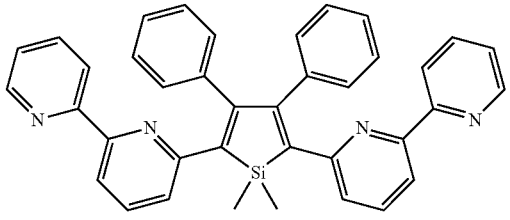 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 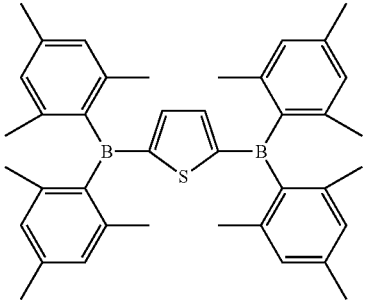 | J. Am. Chem. Soc. 120, 9714 (1998) |
| Fluorinated aromatic compounds | 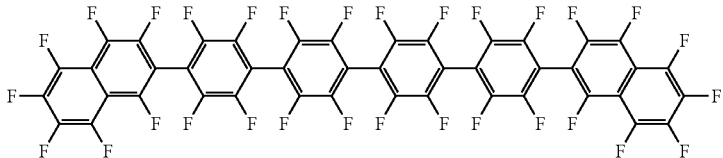 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A composition of matter having the chemical structure:

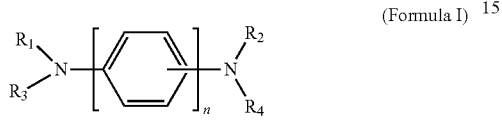

(Formula I)

wherein n is 1, 2 or 3, and the phenyl rings between the nitrogen atoms may be attached to each other and to the nitrogen atoms in a para or meta configuration independently selected for each attachment;

wherein each of $R_1$, $R_2$, $R_3$ and $R_4$ are independently selected from the group consisting of:

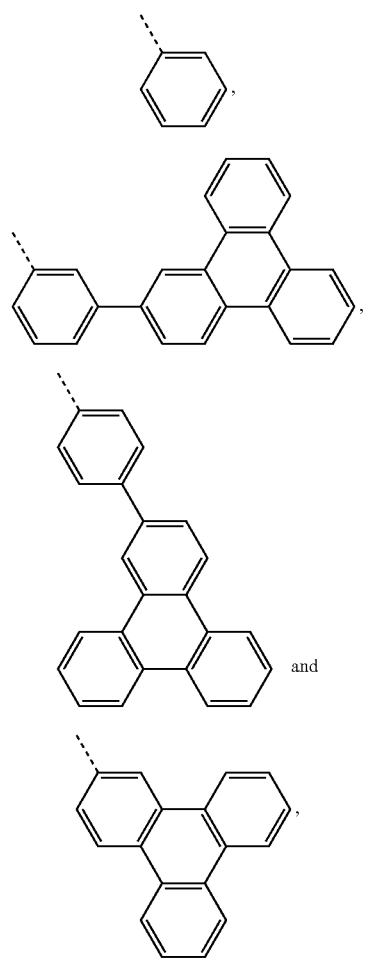

S-1,

S-2,

S-3 and

S-4, wherein the dotted line shows the point of attachment to a nitrogen atom of Formula I;

wherein at least one of $R_1$, $R_2$, $R_3$ and $R_4$ is selected from the group consisting of:

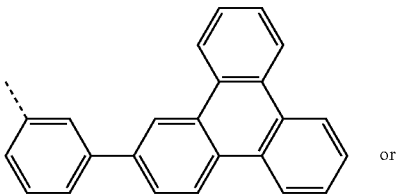

S-2 or

S-3

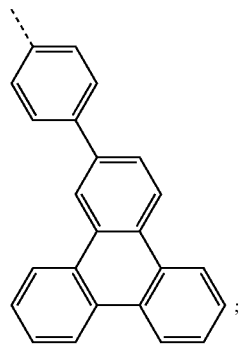

;

wherein $R_1$, $R_2$, $R_3$ and $R_4$ are not all the same; and wherein each of $R_1$, $R_2$, $R_3$ and $R_4$ may be further substituted with substituents that are not fused to $R_1$, $R_2$, $R_3$ and $R_4$.

2. The composition of matter of claim 1, wherein the part of the composition represented by Formula I is more specifically:

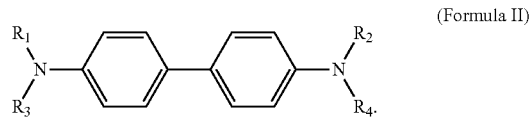

(Formula II)

3. The composition of matter of claim 1, wherein at least one of $R_1$, $R_2$, $R_3$ and $R_4$ is:

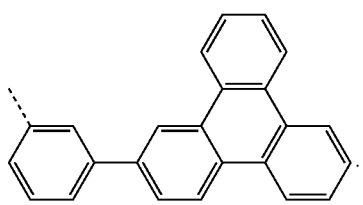

S-2

.

4. The composition of matter of claim 1, wherein at least one of $R_1$, $R_2$, $R_3$ and $R_4$ is:

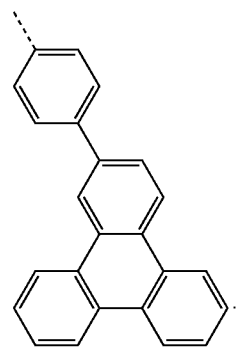

S-3

.

5. The composition of matter of claim 1, wherein at least one of $R_1$, $R_2$, $R_3$ and $R_4$ is:

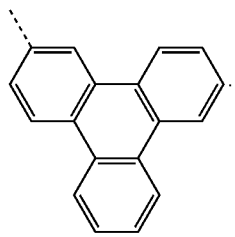

S-4

6. The composition of matter of claim 1, wherein at least one of $R_1$, $R_2$, $R_3$ and $R_4$ is selected from the group consisting of:

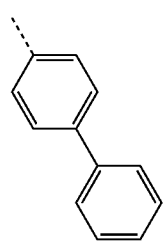

S-5

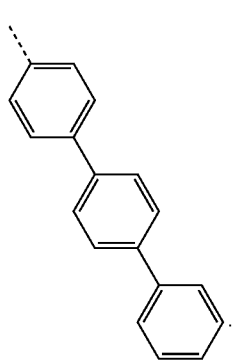

S-6

7. The composition of matter of claim 1, wherein each of $R_1$, $R_2$, $R_3$ and $R_4$ is independently selected from the group consisting of:

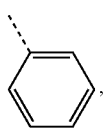

S-1

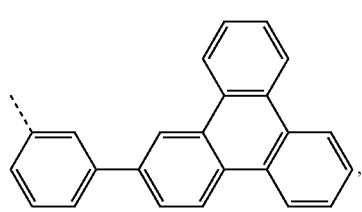

S-2

-continued

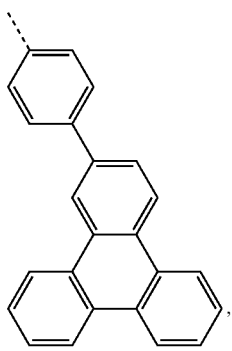

S-3

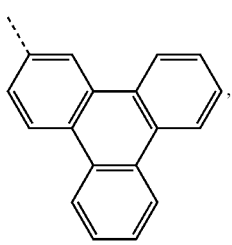

S-4

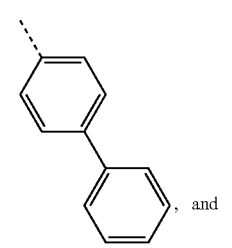

S-5, and

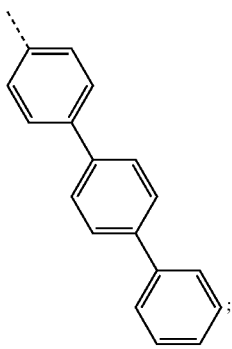

S-6 wherein there are no further substitutions to $R_1$, $R_2$, $R_3$ and $R_4$.

8. The composition of matter of claim 3, wherein the composition of matter has a structure selected from the group consisting of:
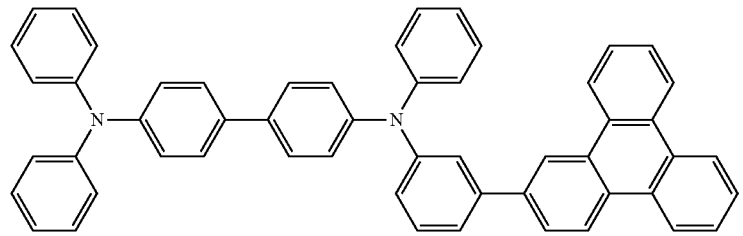
A-1
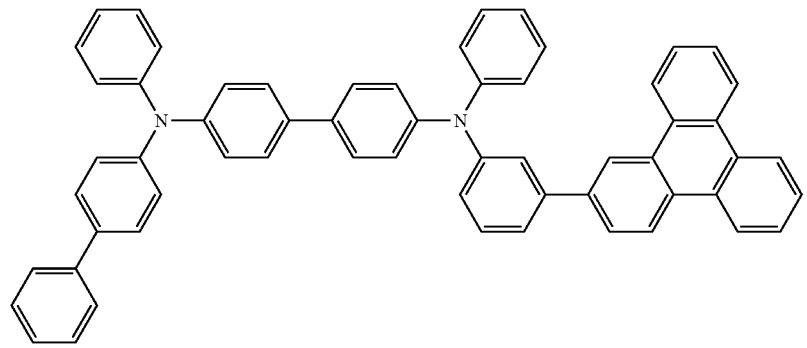
A-2
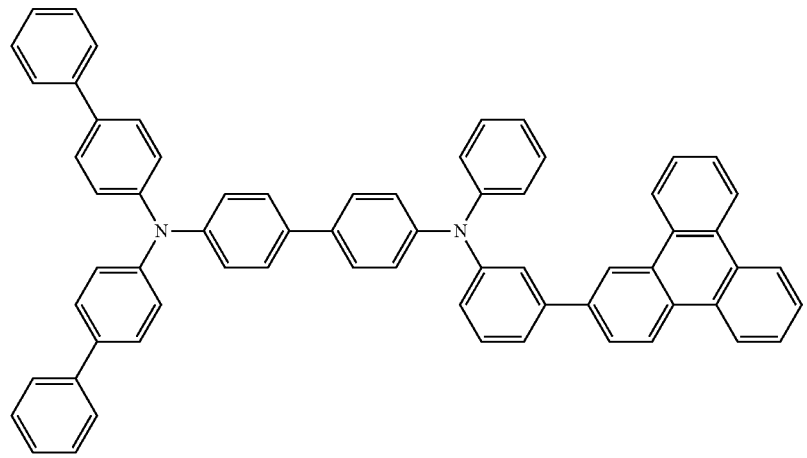
A-3
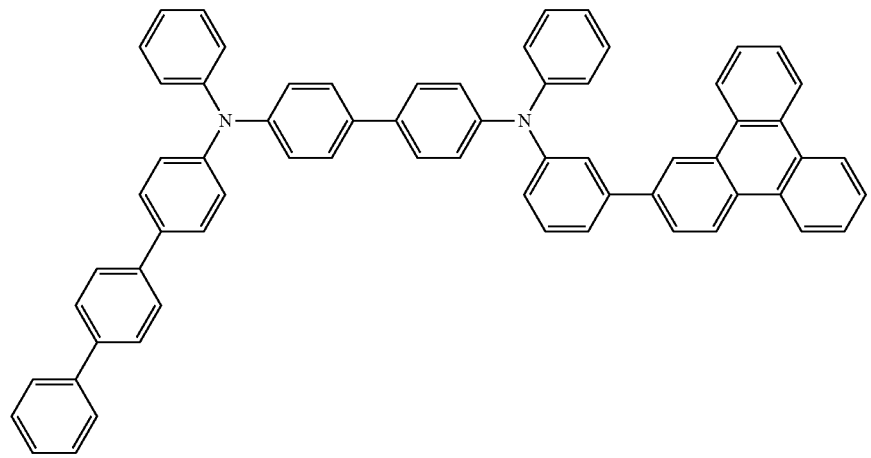
A-4

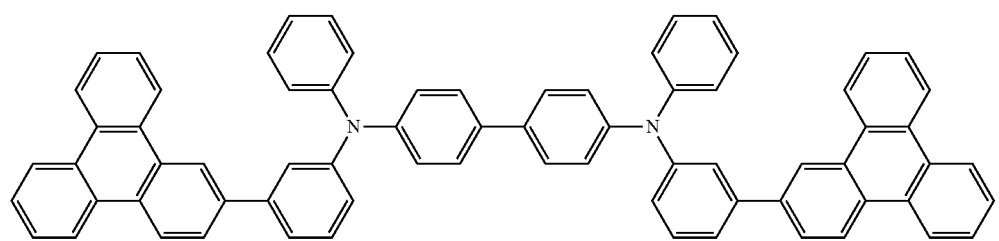
A-5
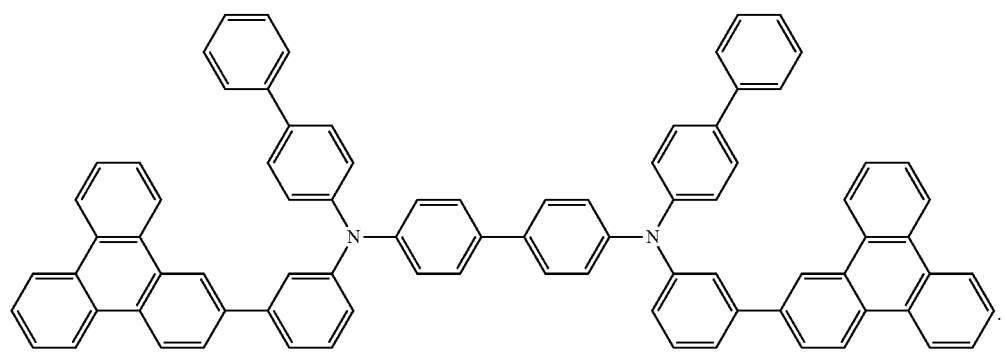
A-6
9. The composition of matter of claim 8, wherein the composition of matter has the structure:
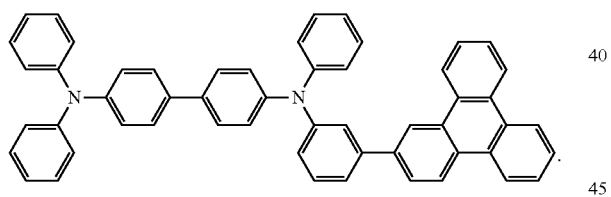
A-1
10. The composition of matter of claim 8, wherein the composition of matter has the structure:
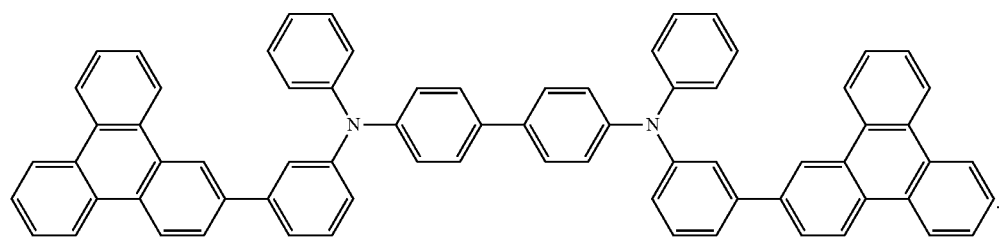
A-5

11. The composition of matter of claim 4, wherein the composition of matter has a structure selected from the group consisting of:

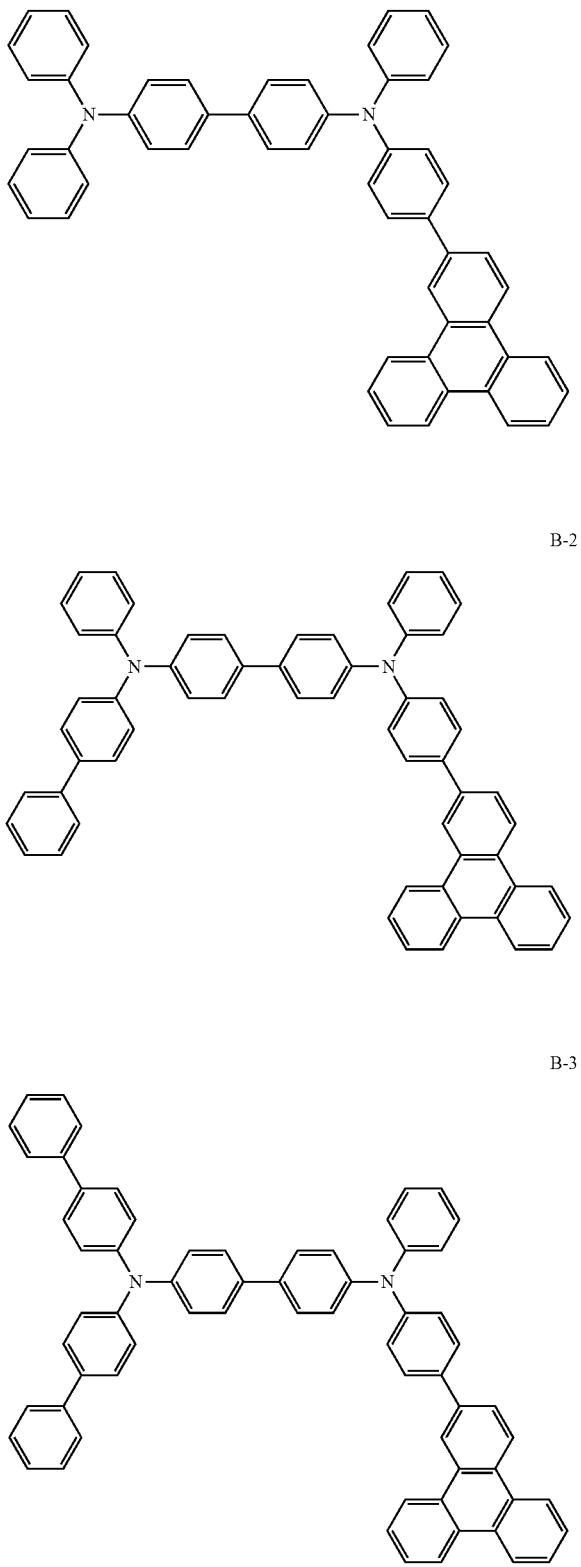

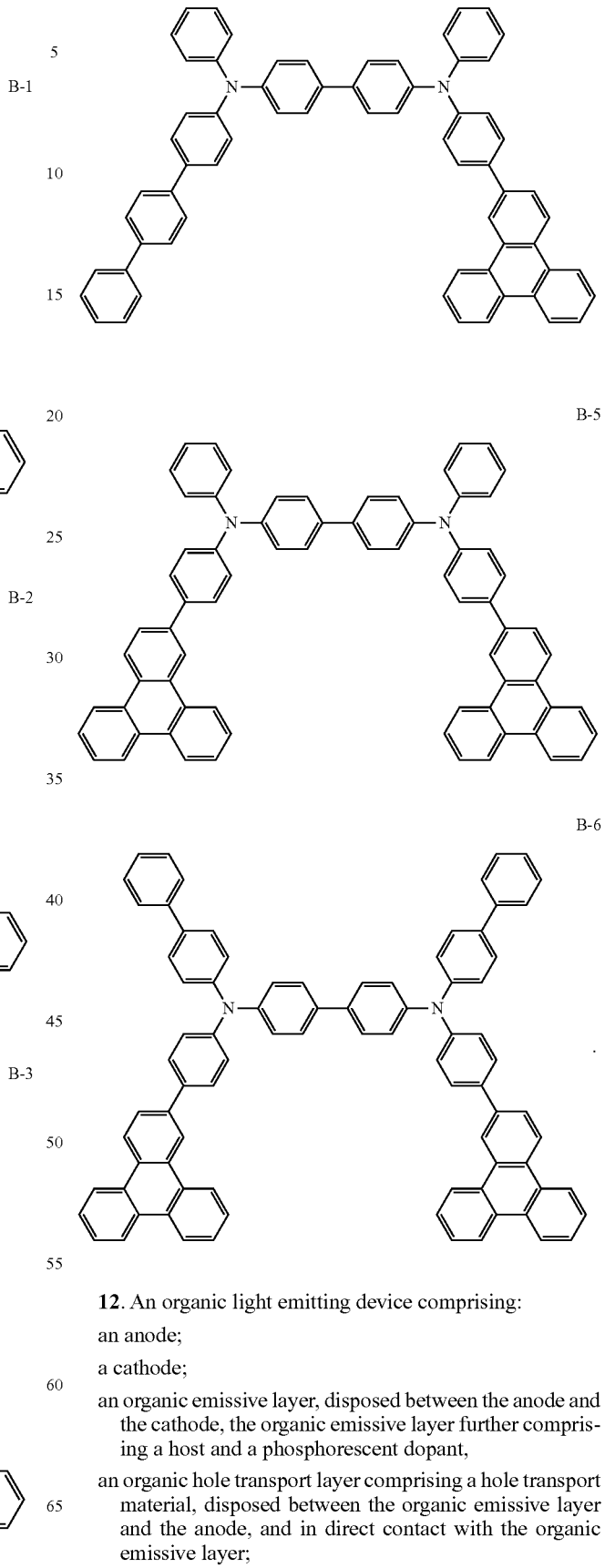

12. An organic light emitting device comprising:

an anode;

a cathode;

an organic emissive layer, disposed between the anode and the cathode, the organic emissive layer further comprising a host and a phosphorescent dopant, an organic hole transport layer comprising a hole transport material, disposed between the organic emissive layer and the anode, and in direct contact with the organic emissive layer;

wherein the hole transport material has the structure:

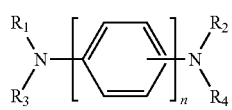
(Formula I)

wherein n is 1, 2 or 3, and the phenyl rings between the nitrogen atoms may be attached to each other and to the nitrogen atoms in a para or meta configuration independently selected for each attachment;

wherein each of $R_1$, $R_2$, $R_3$ and $R_4$ are independently selected from the group consisting of:

S-1

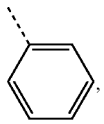,

S-2

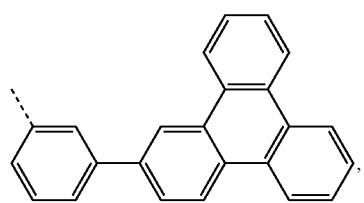,

S-3

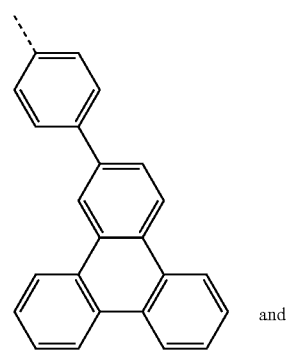

and

S-4

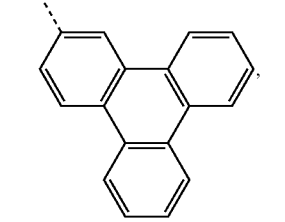, wherein the dotted line shows the point of attachment to a nitrogen atom of Formula I;

wherein at least one of $R_1$, $R_2$, $R_3$ and $R_4$ is selected from the group consisting of:

S-2

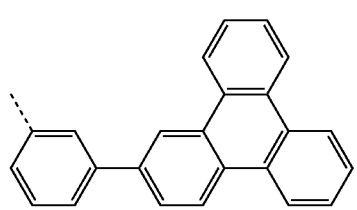

or

S-3

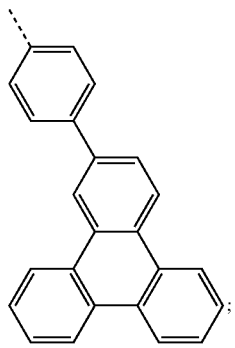;

wherein $R_1$, $R_2$, $R_3$ and $R_4$ are not all the same; and
wherein each of $R_1$, $R_2$, $R_3$ and $R_4$ may be further substituted with substituents that are not fused to $R_1$, $R_2$, $R_3$ and $R_4$.

13. The device of claim 12, wherein the dopant is an organo-metallic iridium material.

14. The device of claim 12, wherein at least one of $R_1$, $R_2$, $R_3$ and $R_4$ is:

S-2

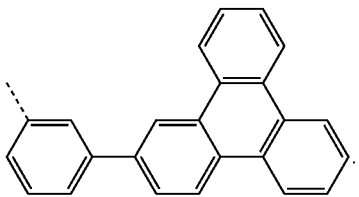.

15. The device of claim 12, wherein at least one of $R_1$, $R_2$, $R_3$ and $R_4$ is:

S-4

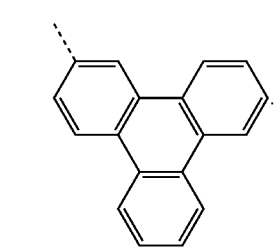.

16. The device of claim 12, wherein the host is a compound comprising a triphenylene containing benzo-fused thiophene.

17. The device of claim 16, wherein the host is:

Compound 3

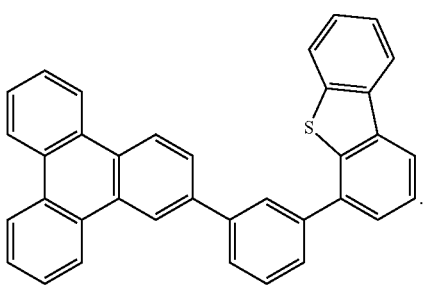.

18. The device of claim 12, wherein the host is an aryltriphenylene compound.

19. The device of claim 18, wherein the host is:

Compound 2

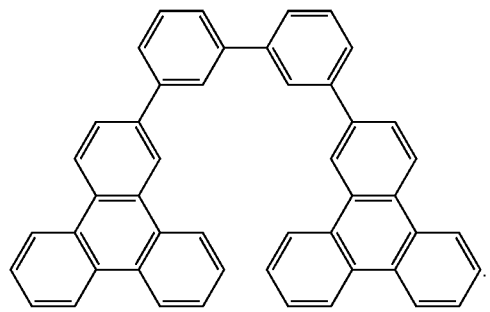

20. A consumer product, wherein the consumer product includes an organic light emitting device that further includes a composition of matter having the chemical structure:

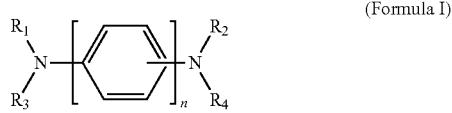
(Formula I)

wherein n is 1, 2 or 3, and the phenyl rings between the nitrogen atoms may be attached to each other and to the nitrogen atoms in a para or meta configuration independently selected for each attachment;

wherein each of $R_1$, $R_2$, $R_3$ and $R_4$ are independently selected from the group consisting of:

S-1

S-2

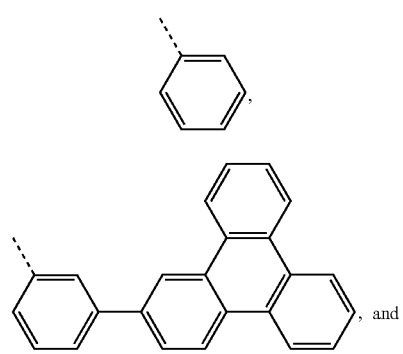
, and

-continued

S-3

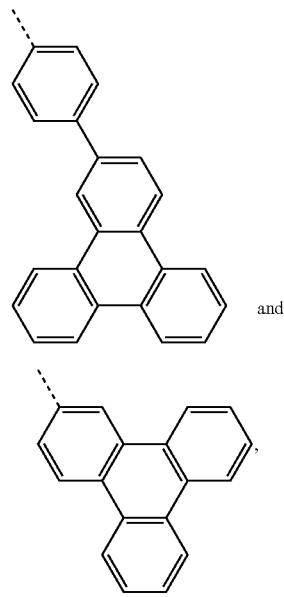
and

S-4 wherein the dotted line shows the point of attachment to a nitrogen atom of Formula I;

wherein at least one of $R_1$, $R_2$, $R_3$ and $R_4$ is selected from the group consisting of:

S-2

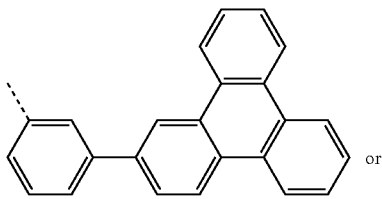
or

S-3

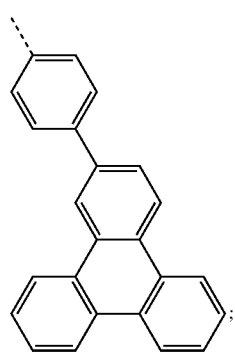
;

wherein $R_1$, $R_2$, $R_3$ and $R_4$ are not all the same; and
wherein each of $R_1$, $R_2$, $R_3$ and $R_4$ may be further substituted with substituents that are not fused to $R_1$, $R_2$, $R_3$ and $R_4$.

* * * * *